US012637653B2

(12) United States Patent (10) Patent No.: US 12,637,653 B2
Snow et al. (45) Date of Patent: May 26, 2026

(54) IN-LINE PRODUCT MONITORING IN INTEGRATED CONTINUOUS BIO-MANUFACTURING

(71) Applicant: Genzyme Corporation, Cambridge, MA (US)

(72) Inventors: Robert Snow, Bridgewater, NJ (US); Joseph P. Kutzko, Bridgewater, NJ (US); Xuezhen Kang, Bridgewater, NJ (US)

(73) Assignee: GENZYME CORPORATION, Cambridge, MA (US)

( * ) Notice: Subject to any disclaimer, the term of this patent is extended or adjusted under 35 U.S.C. 154(b) by 1067 days.

(21) Appl. No.: 17/076,064

(22) Filed: Oct. 21, 2020

(65) Prior Publication Data

US 2021/0115385 A1 Apr. 22, 2021

Related U.S. Application Data

(60) Provisional application No. 62/924,551, filed on Oct. 22, 2019.

(51) Int. Cl.
    C12M 1/36 (2006.01)
    C12M 1/34 (2006.01)
(52) U.S. Cl.
    CPC ............ C12M 41/48 (2013.01); C12M 41/26 (2013.01); C12M 41/30 (2013.01)
(58) Field of Classification Search
    CPC .............. G01N 2021/4153; G01N 2021/8416
    See application file for complete search history.

(56) References Cited

U.S. PATENT DOCUMENTS

| | | | | |
|---|---|---|---|---|
| 3,981,684 | A | 9/1976 | Mavrovic | |
| 5,139,661 | A * | 8/1992 | Kolbert | G01N 21/43 210/198.2 |
| 6,344,172 | B1 * | 2/2002 | Afeyan | G01N 30/62 422/527 |
| 9,650,412 | B2 * | 5/2017 | Konstantinov | C12M 47/12 |
| 10,071,364 | B2 | 9/2018 | Godawat et al. | |
| 10,087,214 | B2 | 10/2018 | Godawat et al. | |
| 2002/0016005 | A1 | 2/2002 | Campbell et al. | |
| 2007/0070330 | A1 | 3/2007 | Chiarello et al. | |
| 2010/0101997 | A1 | 4/2010 | Tateishi | |
| 2010/0230354 | A1 | 9/2010 | Kerr et al. | |
| 2011/0263834 | A1 | 10/2011 | Lees et al. | |
| 2012/0164066 | A1 | 6/2012 | Greene et al. | |
| 2014/0255994 | A1 | 9/2014 | Konstantinov et al. | |
| 2015/0323486 | A1 | 11/2015 | Schick et al. | |
| 2016/0243512 | A1 | 8/2016 | Brandt | |
| 2016/0349220 | A1 | 12/2016 | Laustsen et al. | |
| 2018/0051054 | A1 | 2/2018 | Vetter et al. | |
| 2019/0272894 | A1 | 9/2019 | Wasalathanthri et al. | |
| 2020/0063082 | A1 | 2/2020 | Goh et al. | |
| 2021/0149361 | A1 * | 5/2021 | Jungbauer | G05B 23/0254 |
| 2022/0107269 | A1 | 4/2022 | Liarommatis et al. | |

FOREIGN PATENT DOCUMENTS

| | | |
|---|---|---|
| JP | 2017189123 A | 10/2017 |
| WO | WO 2009/132362 A2 | 10/2009 |
| WO | WO 2014/137903 | 9/2014 |
| WO | 2016041775 A1 | 3/2016 |
| WO | WO 2017/174580 | 10/2017 |

OTHER PUBLICATIONS

C. K. S. Ng et al., Design of High Productivity Sequential Multi-Column Chromatography for Antibody Capture, 92 Food Bioprod. Process. 233-241 (2014).*
F. Steinebach et al., Continuous Counter-Current Chromatography for Capture and Polishing Steps in Biopharmaceutical Production, 11 Biotechnol. J. 1126-1141 (2016).*
J. G. Groetsch, Use of Refractive Index Analyzers for Improved Process Control, 393 Technical Papers—ISA 35-44 (1999).*
Office Action in Canadian Patent Application No. 3,155,216, dated Oct. 26, 2023, 4 pages.
Office Action in Indonesian Patent Application No. P00202205586, dated Nov. 17, 2023, 8 pages (with English translation).
Gebauer et al., "Engineered protein scaffolds as next-generation anitbody therapeutics", Current Opinion in Chemical Biology, 2009, 13:245-255.
Groetsch, "Use of Refractive Index Analyzers for Improved Process Control", Instrument Society of America, Oct. 1999, 393:35-43.
Nebe, "Refractometers, Optical", Encyclopedia of Applied Physics, Jan. 1996, vol. 16, pp. 255-276.
PCT International Search Report and Written Opinion in International Application No. PCT/US2020/056604, dated Jan. 18, 2021, 14 pages.
PCT International Preliminary Report on Patentability in International Application No. PCT/US2020/056604, dated May 5, 2022, 8 pages.
Office Action in Russian Patent Application No. 2022113490, dated Apr. 12, 2024, 16 pages (with English translation).
Japanese Notification of Grounds for Rejection for Japanese Application No. 2022-523568, dated Oct. 8, 2024, 7 pages (with English translation).
Brazilian Search Report for Brazilian Application No. BR112022007525-1 dated Oct. 30, 2025, 4 pages including English translation.

(Continued)

*Primary Examiner* — Randy Boyer
(74) *Attorney, Agent, or Firm* — MH2 Technology Law Group, LLP

(57) ABSTRACT

Methods for controlling a biological manufacturing system include directing a light beam to pass through a wall of a vessel containing a first fluid generated by the biological manufacturing system, measuring an angle of refraction of the light beam in the first fluid, the angle of refraction corresponding to an angle between a propagation direction of the light beam in the first fluid and a normal to an interface between the vessel wall and the first fluid, determining information about the first fluid based on the measured angle of refraction, and adjusting a parameter of the biological manufacturing system based on the information about the first fluid.

12 Claims, 6 Drawing Sheets

(56)                        References Cited

OTHER PUBLICATIONS

Henari, F.Z., et al., "The Influence of pH on Nonlinear Refractive Index of Bromophenol Blue," Physics International, vol. 1, No. 1, 2010, pp. 27-30.

Chinese Office Action and Search Report for Chinese Application No. 202080073635.8, dated Jul. 10, 2024, 22 pages (with English translation).

European Communication Pursuant to Article 94(3) EPC for European Application No. 20807944.2, dated Oct. 9, 2024, 7 pages.

* cited by examiner

IN-LINE PRODUCT MONITORING IN INTEGRATED CONTINUOUS BIO-MANUFACTURING

CROSS-REFERENCE TO RELATED APPLICATIONS

This application claims priority to U.S. provisional patent application 62/924,551, filed on Oct. 22, 2019, the entire contents of which are incorporated herein by reference.

TECHNICAL FIELD

This disclosure relates to product monitoring systems and methods for use in integrated, continuous bio-manufacturing systems.

BACKGROUND

Mammalian cells containing a nucleic acid that encodes a recombinant protein are often used to produce therapeutically or commercially important proteins. Integrated, continuous bio-manufacturing is an important aspect of reducing costs associated with therapies based on such proteins. Monitoring systems are used in bio-manufacturing to assess various biological products.

SUMMARY

Integrated, continuous bio-manufacturing of therapeutic protein substances and other biological molecules hold tremendous promise for future production of life-saving drugs and enhancing widespread adoption of therapies that rely on the availability of such biological molecules. Two-column and multi-column chromatography systems in a variety of configurations can be used for bio-manufacturing on an industrial scale. In such systems, process monitoring of various eluent streams can be used to adjust process-related parameters and to control, for example, the selective collection of eluent streams from certain columns and the adjustment of solution buffer properties (e.g., pH).

This disclosure features methods and systems for determining solution properties such as solute concentrations and pH using rapid, in-line interrogation of solutions emerging from a chromatography column or bio-reactor, or solutions that are fed into such columns or reactors. Angle-resolved refraction measurements are used, together with calibration information, to rapidly and accurately provide quantitative information relating to these solution parameters. The methods can be implemented directly in-line with no sampling of solutions as the solutions flow between vessels, or alternatively, on solution samples drawn from columns, reactors, or transfer lines. Angle of refraction measurements are combined with solution-specific calibration information to yield solution properties, and this information can then be used to control a variety of process-related bio-manufacturing parameters and/or operations.

In an aspect, the disclosure features methods for controlling a biological manufacturing system, the methods including directing a light beam to pass through a wall of a vessel containing a first fluid generated by the biological manufacturing system, measuring an angle of refraction of the light beam in the first fluid, the angle of refraction corresponding to an angle between a propagation direction of the light beam in the first fluid and a normal to an interface between the vessel wall and the first fluid, determining information about the first fluid based on the measured angle of refraction, and adjusting a parameter of the biological manufacturing system based on the information about the first fluid.

Embodiments of the methods can include any one or more of the following features.

The information about the first fluid can include a concentration of a substance in the first fluid and/or a pH value of the first fluid and/or an ionic strength of the first fluid. The first fluid can include a fluid discharged from a purification unit of the system. The purification unit can include at least one chromatography column.

The first fluid can include a feed fluid introduced into a reactor of the system. The first fluid can include a fluid discharged from a filtration unit (e.g., a diafiltration unit) of the system.

The parameter of the biological manufacturing system can include a fluid flow path that selectively directs a successive portion of the first fluid to one of multiple purification units of the system. The parameter of the biological manufacturing system can include a feed rate of a substance into a reactor of the system. The parameter of the biological manufacturing system can include a feed rate of a substance into a diafiltration unit of the system.

The parameter of the biological manufacturing system can include a feed rate of a substance into a purification unit of the system. The parameter of the biological manufacturing system can include a feed rate of successive portions of the first fluid into a purification unit of the system.

The methods can include determining the concentration of the substance from a calibration equation derived from measured calibration data, where the calibration equation expresses the concentration as a function of the angle of refraction. The calibration equation can express the concentration as a linear function of the angle of refraction. The calibration equation can express the concentration as a nonlinear function of the angle of refraction. The methods can include transmitting the concentration information to a controller of the system, where the controller is configured to receive the concentration information and to adjust the parameter of the system.

The substance can include a protein and/or a recombinant protein-based drug product and/or a nucleic acid-based product.

The first fluid can be a process fluid generated by the system as part of a biological manufacturing process. The first fluid can include an eluate discharged from a chromatography column. The first fluid can include an eluate solution from a first purification unit of the system and the information can include a concentration of a substance in the first fluid, and the parameter adjustment can include directing eluate solution from the first purification unit into an inlet of a second purification unit when the concentration of the substance in the first fluid exceeds a threshold value. The first and second purification units can each include at least one chromatography column.

The first fluid can include an eluate solution from a first purification unit of the system, the information can include a concentration of a substance in the first fluid, and an inlet of the first purification unit can be connected to a conduit that delivers a feed solution to the first purification unit, and the methods can include, when a concentration of the substance in the first fluid exceeds a threshold value, disconnecting the inlet of the first purification unit from the conduit, and connecting an inlet of a second purification unit of the system to the conduit to deliver the feed solution to the second purification unit.

The methods can include directing a second light beam to pass through a wall of a second vessel containing a second fluid generated by the biological manufacturing system, measuring an angle of refraction of the second light beam in the second fluid, the angle of refraction corresponding to an angle between a propagation direction of the second light beam in the second fluid and a normal to an interface between the wall of the second vessel and the second fluid, determining information about the second fluid based on the measured angle of refraction of the second light beam, and adjusting a second parameter of the biological manufacturing system based on the information about the second fluid. The information about the second fluid can include a concentration of a buffer solution component in the second fluid. The information about the second fluid can include a concentration of an ionic compound or a dissolved salt thereof in the second fluid. Adjusting the second parameter can include adjusting a feed rate of the second fluid into a purification unit of the system.

The methods can include repeating the directing, measuring, determining, and transmitting steps to provide the concentration information as a feedback signal to the controller to adjust the parameter of the system during a biological manufacturing process.

Embodiments of the methods can also include any of the other features or steps described herein, including combinations of features and/or steps individually described in connection with the same or different embodiments, in any combination except as expressly stated otherwise.

In another aspect, the disclosure features biological manufacturing systems that include a vessel configured to hold or transport a first fluid generated by the systems and featuring a wall defining at least a portion of the vessel, a light source configured to direct a light beam to pass through the wall, a detector configured to measure an angle of refraction of the light beam in the first fluid, the angle of refraction corresponding to an angle between a propagation direction of the light beam in the first fluid and a normal to an interface between the wall and the first fluid, and a first controller connected to the detector and configured to: receive information about the angle of refraction from the detector, and to determine information about the first fluid based on the measured angle of refraction; and adjust a parameter of the system based on the information about the first fluid.

Embodiments of the systems can include any one or more of the following features.

The information about the first fluid can include a concentration of a substance in the first fluid and/or a pH value of the first fluid.

The systems can include a purification unit, where the first fluid includes a fluid discharged from the purification unit. The purification unit can include at least one chromatography column. The systems can include a reactor, where the first fluid includes a feed fluid introduced into the reactor. The systems can include a filtration unit (e.g., a diafiltration unit), where the first fluid includes a fluid discharged from the filtration (e.g., diafiltration) unit.

The systems can include multiple purification units, where the parameter of the system includes a fluid flow path that selectively directs a successive portion of the first fluid to one of the multiple purification units. The systems can include a reactor, where the parameter of the system includes a feed rate of a substance into the reactor. The systems can include a filtration (e.g., diafiltration) unit, where the parameter of the system includes a feed rate of a substance into the filtration (e.g., diafiltration) unit. The systems can include a purification unit, where the parameter of the system includes a feed rate of a substance into the purification unit. The systems can include a purification unit, where the parameter of the system includes a feed rate of successive portions of the first fluid into the purification unit.

The first controller can be configured to determine the concentration of the substance from a calibration equation derived from measured calibration data, where the calibration equation expresses the concentration as a function of the angle of refraction. The calibration equation can express the concentration as a linear function of the angle of refraction. The calibration equation can express the concentration as a nonlinear function of the angle of refraction.

The substance can include a protein. The substance can include a recombinant protein-based drug product. The substance can include a nucleic acid-based product.

The first fluid can be a process fluid generated by the system as part of a biological manufacturing process. The systems can include a purification unit, where the first fluid includes an eluate discharged from the purification unit.

The systems can include a first purification unit and a second purification unit, where the first fluid includes an eluate solution from the first purification unit, the information includes a concentration of a substance in the first fluid, and the parameter adjustment can include directing eluate solution from the first purification unit into an inlet of the second purification unit when the concentration of substance in the first fluid exceeds a threshold value. The first and second purification units can each include at least one chromatography column.

The systems can include a first purification unit and a second purification unit, the first purification unit featuring an inlet connected to a conduit that delivers a feed solution to the first purification unit, where the first fluid includes an eluate solution from the first purification unit, the information includes a concentration of a substance in the first fluid, and the parameter adjustment includes disconnecting the inlet of the first purification unit from the conduit and connecting an inlet of the second purification unit to the conduit to deliver the feed solution to the second purification unit when the concentration of the substance in the first fluid exceeds a threshold value.

The systems can include a second vessel configured to hold or transport a second fluid generated by the system and featuring a second wall defining at least a portion of the second vessel, a second light source configured to direct a second light beam to pass through the second wall, and a second detector configured to measure an angle of refraction of the second light beam in the second fluid, the angle of refraction corresponding to an angle between a propagation direction of the second light beam in the second fluid and a normal to an interface between the second wall and the second fluid, where the first controller is connected to the second detector and configured to: receive information about the angle of refraction from the second detector, and to determine information about the second fluid based on the measured angle of refraction; and adjust a second parameter of the system based on the information about the second fluid.

The information about the second fluid can include a concentration of a buffer solution component in the second fluid. The information about the second fluid can include a concentration of an ionic compound or a dissolved salt thereof in the second fluid.

The systems can include a purification unit, where adjusting the second parameter includes adjusting a feed rate of the second fluid into the purification unit.

During a biological manufacturing process, the light source can be configured to repeatedly direct the light beam to pass through the wall, the detector can be configured to repeatedly measure the angle of refraction of the light beam in the first fluid, and the first controller can be configured to repeatedly: receive information about the angle of refraction from the detector; determine information about the first fluid based on the measured angle of refraction; and adjust the parameter of the system based on the information about the first fluid.

The systems can include multiple purification units each having at least one chromatography column, a column switching mechanism, and a second controller connected to the column switching mechanism and in communication with the first controller, where the first controller is configured to adjust the parameter of the system by transmitting a signal to the second controller causing the second controller to adjust the column switching mechanism to selectively direct a fluid into one of the multiple purification units. The selectively directed fluid can include an additional portion of the first fluid.

The systems can include a reservoir containing a second fluid and a second controller in communication with the first controller, where the first controller is configured to adjust the parameter of the system by transmitting a control signal to the second processor based on the information about the first fluid, and the second controller is configured to introduce a portion of the second fluid from the reservoir into a successive portion of the first fluid in response to the control signal. The second fluid can include a buffer solution. The second fluid can include a solution of an ionic compound or a dissolved salt thereof.

Embodiments of the systems can also include any of the other features or steps described herein, including combinations of features and/or steps individually described in connection with the same or different embodiments, in any combination except as expressly stated otherwise.

Unless otherwise defined, all technical and scientific terms used herein have the same meaning as commonly understood by one of ordinary skill in the art to which this disclosure belongs. Although methods and materials similar or equivalent to those described herein can be used in the practice or testing of the subject matter herein, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments are set forth in the accompanying drawings and the description below. Other features and advantages will be apparent from the description, drawings, and claims.

DESCRIPTION OF DRAWINGS

Like symbols in the drawings indicate like elements.

DETAILED DESCRIPTION

Introduction

Industrial scale bio-manufacturing can be performed with intermediate and/or product purification in two-column and multi-column chromatography systems in a variety of configurations. In these complex systems, product yield, purity, and waste rates are functions of a large number of process-related parameters and steps. During manufacturing of therapeutic proteins and other commercially valuable bio-molecules, product outcomes can be strongly influenced by these parameters and steps. Appropriate control over such parameters and steps is therefore an important aspect of large scale manufacturing. Features and aspects of bio-manufacturing systems are disclosed, for example, in PCT Patent Application Publication No. WO 2014/137903, the entire contents of which are incorporated herein by reference.

Exercising appropriate control over bio-manufacturing parameters, including automated control, is facilitated by in-process, in-line monitoring of intermediate solution streams, and specifically, concentrations of intermediates and products in such streams, and other properties (such as pH, for example) of such streams. Conventional methods for solution monitoring include techniques such as UV absorbance measurements. Unfortunately, however, such methods are subject to drift over measurement periods of a few days due to factors such as temperature, humidity, ambient light intensities, and local sample inhomogeneity.

Disclosed herein are methods and systems that use angle-resolved refraction measurements to determine properties of process solutions, including product and intermediate component concentrations and buffer concentrations/pH levels. Such refraction measurements are rapid, highly reproducible, and can be used to determine accurate quantitative information about the solutions when combined with suitable calibration information. This quantitative information can in turn be used as feedback to automated or semi-automated process control systems that adjust process conditions and initiate or discontinue certain process steps.

In-Line Angle-Resolved Refraction Measurements

Figure 1:
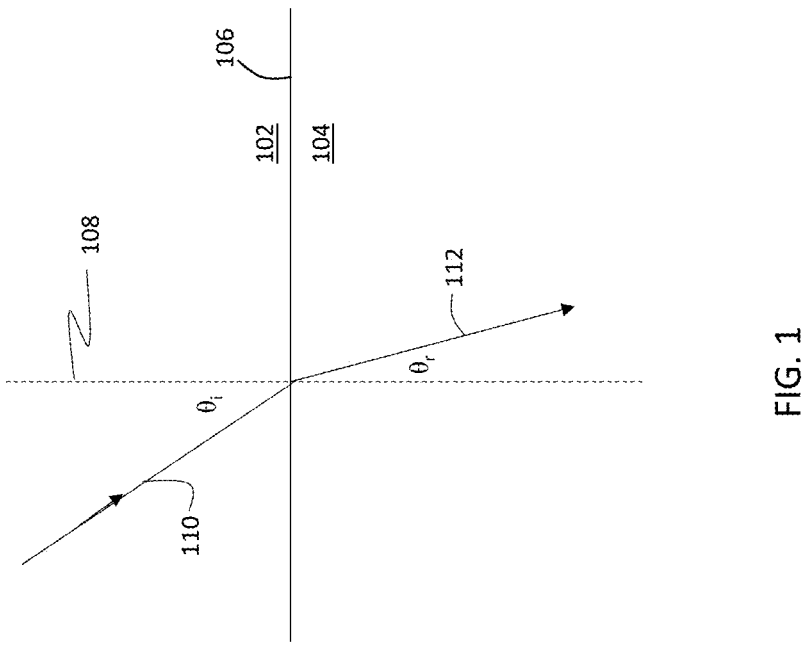
FIG. 1 is a schematic diagram showing a light beam crossing an interface between two materials and refracting at the interface.

FIG. 1 is a schematic diagram showing a beam of light passing from a gaseous environment (e.g., air) into a liquid environment (e.g., an aqueous solution). In FIG. 1, an interface 106 separates the gaseous environment 102 from the liquid environment 104. Incident light beam 110 propagates through gaseous environment 102, passes through interface 106, and then propagates through liquid environment 104 as refracted beam 112. Incident light beam 110 is incident on interface 106 at an angle $\theta_i$ relative to a normal 108 to interface 106. Refracted light beam 112 forms an angle $\theta_r$ with normal 108.

The refraction angle $\theta_r$ depends on the incidence angle $\theta_i$, and the indices of refraction, $n_{gas}$ and $n_{liquid}$, of the gaseous and liquid environments, respectively. The relationship between these variables is Snell's Law:

$$n_{gas} \sin(\theta_i) = n_{liquid} \sin(\theta_r) \qquad [1]$$

Thus, rearranging Equation (1), $\theta_r$ can be calculated as:

$$\theta_r = \sin^{-1}(n_{gas} \sin \theta_i / n_{liquid}) \qquad [2]$$

$\theta_r$ can be determined from Equation (2) when $n_{liquid}$ is known. Values of $n_{liquid}$ have been measured for a wide variety of pure liquids. For a solution consisting of a solute dissolved in a solvent, the refractive index $n_{solution} \approx n_{solvent} + \Delta n_{solute}$, where $\Delta n_{solute}$ represents an additional contribution to the refractive index of the solution arising from the presence of the solute. In general, a dissolved solute makes a solution more optically dense than the pure liquid solvent, which implies that $n_{solution} > n_{solvent}$ in most cases.

As the concentration of solute in a solution increases, the optical density and refractive index of the solution also typically increase. There is no general analytical form that describes the relationship between the concentration of a particular solute in a particular solvent and the refractive index of the resulting solution. Instead, only the following general relationship holds:

$$n_{solution} = f(c) \qquad [3]$$

where c is the concentration of a particular solute in a particular solvent that forms the solution, and f(c) is an unknown functional form.

If it is assumed that f(c) is a linear function such that f(c)=uc+v, where u and v are unknown constants, then $$n_{solution} = uc + v \qquad [4]$$

Substituting into Equation (1) yields $$n_{gas} \sin \theta_i = (uv + c) \sin \theta_r \qquad [5]$$

Rearranging Equation (5) for the solute concentration c yields the following expression:

$$c = \left( \frac{n_{gas}}{u} \right) \sin\theta_i \csc\theta_r - \left( \frac{v}{u} \right) \qquad [6]$$

Equation (6) expresses the concentration c as a linear function of $\csc(\theta_r)$, in the form $c = m \cdot \csc(\theta_r) + b$, with slope $m = (n_{gas}/u) \cdot \sin(\theta_i)$ and intercept $b = -(v/u)$. If, for certain values of $\theta_r$, the condition $\csc(\theta_r)\ \theta_r$ holds, then $$c = m \cdot \theta_r + b \qquad [7]$$

with the values of m and b as above. In other words, if values of the constants m and b are known, for example from calibration information for a particular solute dissolved in a particular solvent, then for a solution of an unknown concentration of the solute dissolved in the solvent, the solute concentration c can be determined directly from Equation (7) and a measurement of the refraction angle $\theta_r$.

Figure 2:
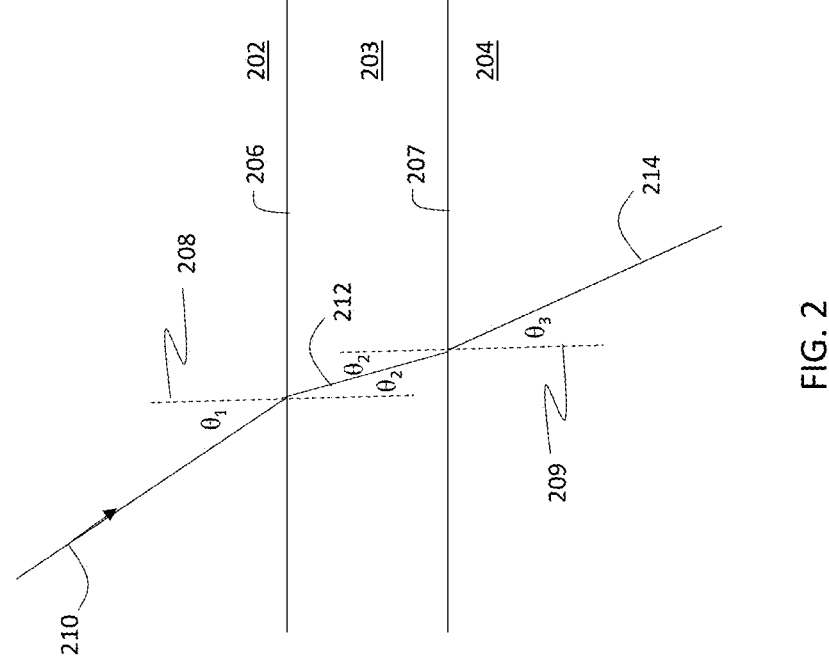
FIG. 2 is a schematic diagram showing a light beam crossing interfaces between different materials and refracting at the interfaces.

The situation is slightly more complicated when the interrogating beam of light passes through the wall of a vessel or conduit in which the solution is held or is flowing. FIG. 2 is a schematic diagram showing a light beam 210 propagating through a gas 202. The beam is directed through a solid, translucent or transparent wall 203 of a tube or vessel that contains a liquid 204. An interface 206 separates gas 202 from solid wall 203, and a second interface 207 separates solid wall 203 from liquid 204. Gas 202 has an index of refraction $n_{gas}$, solid wall 203 is formed of a material that has an index of refraction $n_{solid}$, and liquid 204 has an index of refraction $n_{liquid}$.

Light beam 210 is incident on interface 206 at an angle $\theta_1$ with respect to normal 208 to interface 206, and refracts within solid wall 203 at an angle $\theta_2$ relative to normal 208, forming refracted beam 212. With the assumption that interfaces 206 and 207 are parallel, refracted beam 212 is incident on interface 207 at an angle $\theta_2$ relative to normal 209 to interface 207, and refracts within liquid 204 at an angle $\theta_3$ relative to normal 209, forming refracted beam 214.

At interface 206, Snell's Law describes the following relationship between the indices of refraction and the incidence and refraction angles:

$$n_{gas} \sin \theta_1 = n_{solid} \sin \theta_2 \qquad [8]$$

Similarly, at interface 207, Snell's Law yields:

$$n_{solid} \sin \theta_2 = n_{liquid} \sin \theta_3 \qquad [9]$$

Combining Equations (8) and (9) eliminates the dependence on solid wall 203:

$$n_{gas} \sin \theta_1 = n_{liquid} \sin \theta_3 \qquad [10]$$

Equation (10) has the same form as Equation (1), with $\theta_i = \theta_1$ and $\theta_r = \theta_3$. Accordingly, for a particular solute dissolved in a particular solvent to form liquid 204, the concentration c of the dissolved solute, with the same corresponding assumptions as above, can be expressed as:

$$c = m \cdot \theta_3 + b \qquad [11]$$

where the slope $m = (n_{gas}/u) \cdot \sin(\theta_1)$ and intercept $b = -(v/u)$. In other words, if the values of the constants m and b are known, e.g., from calibration data, then the concentration c can be determined directly from a measurement of refraction angle $\theta_3$ and Equation (11).

Figure 3:
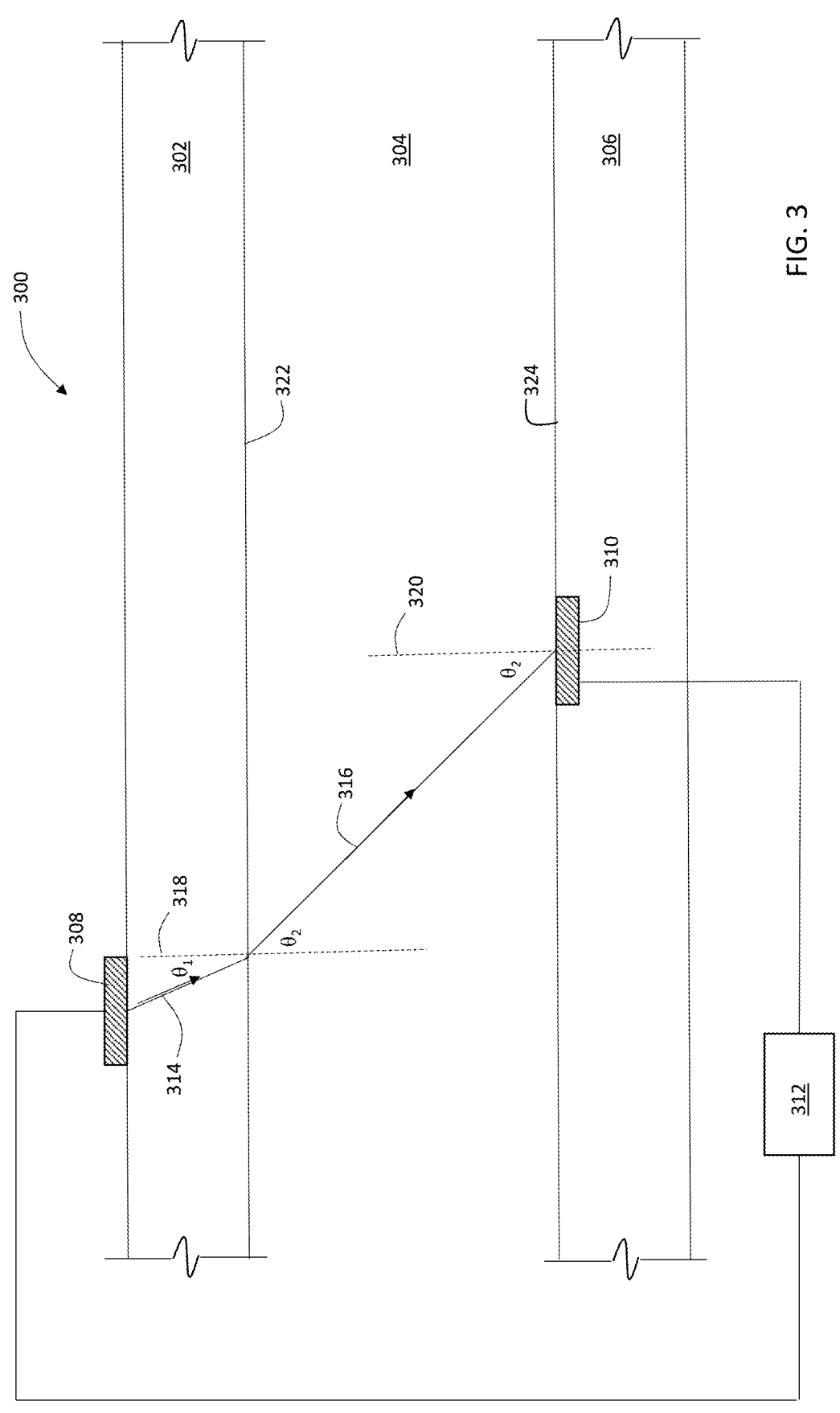
FIG. 3 is a schematic diagram showing a system for performing angle-resolved refraction measurements for a light beam.

FIG. 3 is a schematic diagram showing an embodiment of a measurement system 300 for measuring a refraction angle of a light beam in a liquid. System 300 includes a light source 308 and an angle-resolving light detector 310 coupled to a controller 312. Liquid 304, for example an intermediate or product solution that includes an amount of a bio-manufactured product such as a protein dissolved in a solvent, is contained between walls 302 and 306 of a vessel or conduit. Liquid 304 can be stationary within the vessel or conduit, or moving, i.e., flowing. Walls 302 and 306 are formed from a solid, translucent or transparent material such as glass or a polymer material, and have refractive index $n_{wall}$. Liquid 304 has refractive index $n_{solution}$.

During operation, controller 312 directs light source to generate an incident light beam 314 that is incident on the interface 322 between wall 302 and liquid 304 at an angle $\theta_1$ relative to the normal 318 to interface 322. Refracted beam 316 refracts at an angle $\theta_2$ relative to normal 318.

Refracted beam 316 is incident on detector 310 positioned at interface 324, at an angle of $\theta_2$ relative to interface normal 320. Detector 310 is configured to measure the refraction angle $\theta_2$ of beam 316, and to transmit information about $\theta_2$ to controller 312. The geometric arrangement in FIG. 3 is similar to the arrangement in FIG. 1, with $\theta_i = \theta_1$ and $\theta_r = \theta_2$. Accordingly, Snell's Law gives:

$$n_{wall} \sin \theta_1 = n_{solution} \sin \theta_2 \qquad [12]$$

Thus, for a particular solute dissolved in a particular solvent to form liquid 304, the concentration c of the dissolved solute, with the same corresponding assumptions as above, can be expressed as:

$$c = m \cdot \theta_2 + b \qquad [13]$$

where the slope $m=(n_{wall}/u)\cdot\sin(\theta_1)$ and intercept $b=-(v/u)$. That is, if the values of the constants m and b are known, e.g., from calibration data, then the concentration c can be determined directly from a measurement of refraction angle $\theta_2$ and Equation (13).

Figure 4:
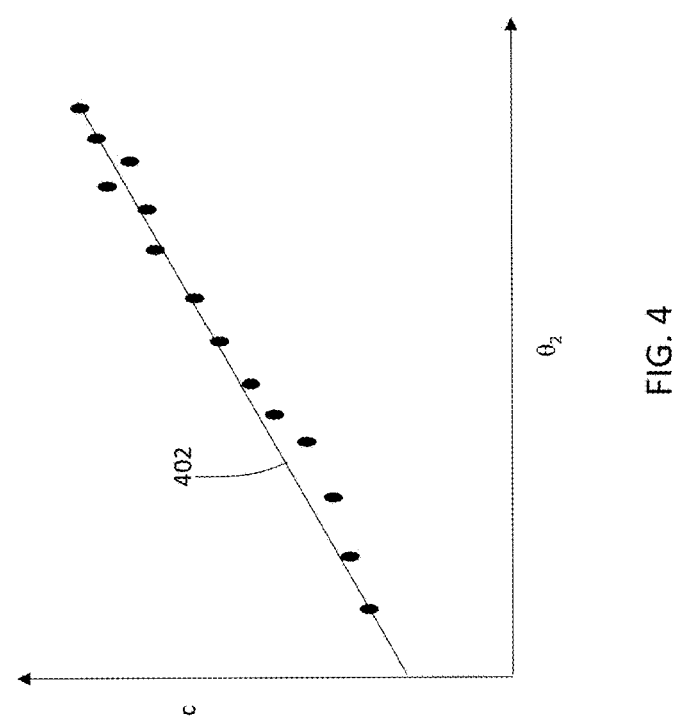
FIG. 4 is a schematic plot showing solute concentration values as a function for refraction angle for a solution.

To obtain a quantitative concentration c of a particular solute in a particular solvent, calibration data is first measured. Typically, for a series of solutions, each of which has a known concentration of the solute of interest dissolved in the solvent of interest, each solution is measured using system 300 to generate a set of calibration data that includes solute concentrations c and corresponding refraction angles $\theta_2$. FIG. 4 is a schematic plot showing a set of measured refraction angles $\theta_2$ for solutions of known concentration c of a particular solute.

After the data have been measured, the data are transmitted to controller 312 for analysis. Controller 312 is configured to determine the values of constants m and b in Equation (13). In some embodiments, for example, controller 312 performs a linear regression analysis to determine a line of best fit 402 through the set of $(c, \theta_2)$ calibration data points. The regression analysis determines values of the constants m and b from Equation (13). Once the values of m and b have been determined, system 300 is calibrated and is ready for in-line measurement of process solutions in a bio-manufacturing system.

Figure 5:
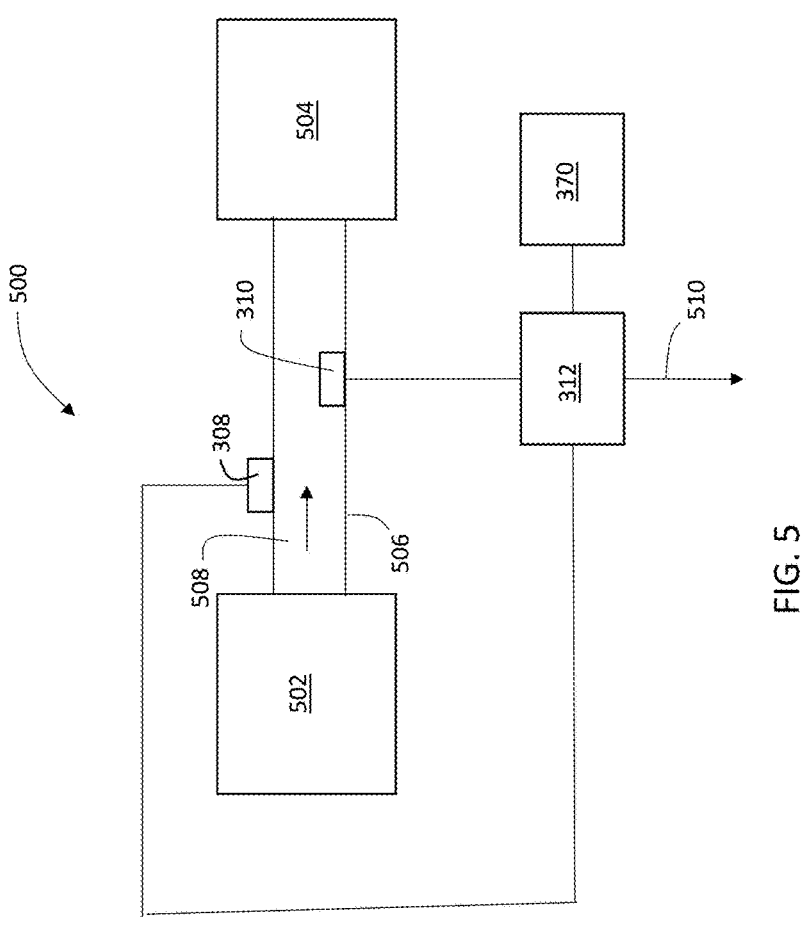
FIG. 5 is a schematic diagram showing an in-line system for performing angle-resolved refraction measurements for a light beam.

FIG. 5 is a schematic diagram of a portion of a bio-manufacturing system 500 that includes measurement system 300. In FIG. 5, a process solution 508 containing a product or intermediate species, such as a protein, polypeptide, antibody, or another biological molecule (i.e., a solute) dissolved in a solvent, flows from a first vessel 502 (e.g., a chromatography column, a bio-reactor or other reaction or purification vessel, or a tank) to a second vessel 504 (e.g., a chromatography column, a bio-reactor or other reaction or purification vessel, or a tank) through a conduit 506. Integrated into conduit 506 are a light source 308 and angle-resolved detector 310 connected to controller 312. As shown in FIG. 5, controller 312 also includes a connection 510 to another control/logic unit that adjusts various operating parameters and/or process steps associated with the bio-manufacturing process.

During operation, as discussed above, controller 312 includes calibration information (i.e., values of m and b) determined for the product or intermediate species dissolved in the solute. In some embodiments, controller 312 determines this information prior to making in-line measurements on solution 508. Alternatively, in certain embodiments, the calibration information is retrieved by controller 312 from a storage unit 370 (e.g., a memory unit or other persistent storage medium such as a magnetic or optical storage medium). As another alternative, in some embodiments, the calibration information is encoded within controller 312, e.g., in the firmware of the controller. As a further example, in certain embodiments, the calibration information is stored in a network-accessible database, and controller 312 is configured to retrieve the calibration information from the database via a wired or wireless network interface (e.g., an interface to a local area network, a wide area network, or any other type of distributed network architecture connecting two or more computing devices).

To measure solution 508, light source 308 generates a light beam that refracts as it passes into solution 508, and detector 310 measures the angle of refraction $\theta_2$. Controller 312 receives the information about refraction angle $\theta_2$ from detector 310 and then uses the angle information and the calibration information in Equation (13) to determine the concentration c of the product or intermediate species in solution 508. Optionally, controller 312 can communicate the concentration information for solution 508 to another control/logic unit via connection 510.

In general, conduit 506 is formed from a material that is transparent or translucent to the light beam generated by light source 308. In some embodiments, for example, conduit 506 is formed from a flexible polymer material such as, but not limited to, polyethylene, polypropylene, or polybutylene. In certain embodiments, conduit 506 can be formed of one or more glass materials.

A wide variety of devices can be used to implement light source 308. In some embodiments, for example, light source 308 features one or more light emitting diodes (LEDs). Alternatively, or in addition, in certain embodiments, light source 308 includes one or more laser diodes. In some embodiments, light source 308 includes one or more lasers (e.g., gas lasers, solid state lasers, organic dye-based lasers). In certain embodiments, light source 308 includes one or more fluorescent and/or incandescent sources, such as flash-lamp-based sources.

Light source 308 can be configured to generate a light beam having a central wavelength in various spectral regions. In some embodiments, for example, the light beam has a central wavelength in the visible region of the spectrum, from about 400 nm to about 800 nm. In certain embodiments, the light beam has a central wavelength in the near-infrared or infrared region of the spectrum, at a wavelength greater than 800 nm. In some embodiments, the light beam has a central wavelength in the ultraviolet region of the spectrum, at a wavelength less than 400 nm. Wavelengths in the visible region of the spectrum can be advantageous in that they are readily observable for adjustment and calibration of measurement system 300. Wavelengths in the near-infrared and infrared region of the spectrum can be advantageous in that they may at least partially pass through materials that are otherwise relative opaque to wavelengths in the visible region of the electromagnetic spectrum.

In some embodiments, light source 308 is a relatively broadband light source and generates a light beam having a full width at half maximum (FWHM) spectral bandwidth of 5 nm or more (e.g., 7 nm or more, 10 nm or more, 12 nm or more, 15 nm or more, 20 nm or more, 25 nm or more, 30 nm or more, 50 nm or more). In certain embodiments, light source 308 is a relatively narrowband light source and generates a light beam having a FWHM spectral bandwidth of 3 nm or less (e.g., 2 nm or less, 1 nm or less, 0.5 nm or less).

In general, any sensor capable of performing angle-resolved measurements of light passing through solution 508 can be used in detector 310. That is, a wide variety of sensors capable of measuring the refraction angle $\theta_2$ for a light beam passing through solution 508 can be used. As one example, in certain embodiments, detector 310 can include the InVue® CR288 concentration monitor (available from Entegris, Inc., Billerica, MA).

In FIG. 5, light source 308 is in contact with the surface of conduit 506, and the light beam generated by light source 308 is coupled directly into the wall of conduit 506. More generally, however, light source 308 does not have to be in direct contact with conduit 506 and can be spaced from conduit 506. If light source 308 is spaced from conduit 506 such that the light beam propagates through a gas (e.g., air) before entering the conduit wall, then relations similar to Equations (12) and (13) still hold, with $n_{gas}$ in place of $n_{wall}$ and $\theta_1$ referring to the light beam's angle of incidence on the conduit wall.

In FIGS. 3 and 5, detector 310 is integrated into the wall 306 of a vessel or conduit containing the solution to be analyzed, at a location approximately opposite to (and laterally displaced from) light source 308. Measurement system 300 thus performs a transmission mode measurement of the light beam refracted through solution 508.

Either or both of light source 308 and detector 310 can optionally be integrated into the wall of a vessel or conduit containing the solution to be analyzed. A variety of different implementations can be used to integrate these components into the vessel wall. For example, in some embodiments, the vessel wall includes an aperture dimensioned to receive light source 308 or detector 310. Light source 308 or detector 310 can be positioned within the aperture, and fixed in position using a suitable adhesive. In certain embodiments, light source 308 or detector 310 is positioned within the aperture so that the surface of the light source 308 or detector 310 that projects through the vessel wall is aligned flush with an interior surface of the vessel wall so that solution flowing within the vessel is not impeded by the light source or detector.

Figure 6:
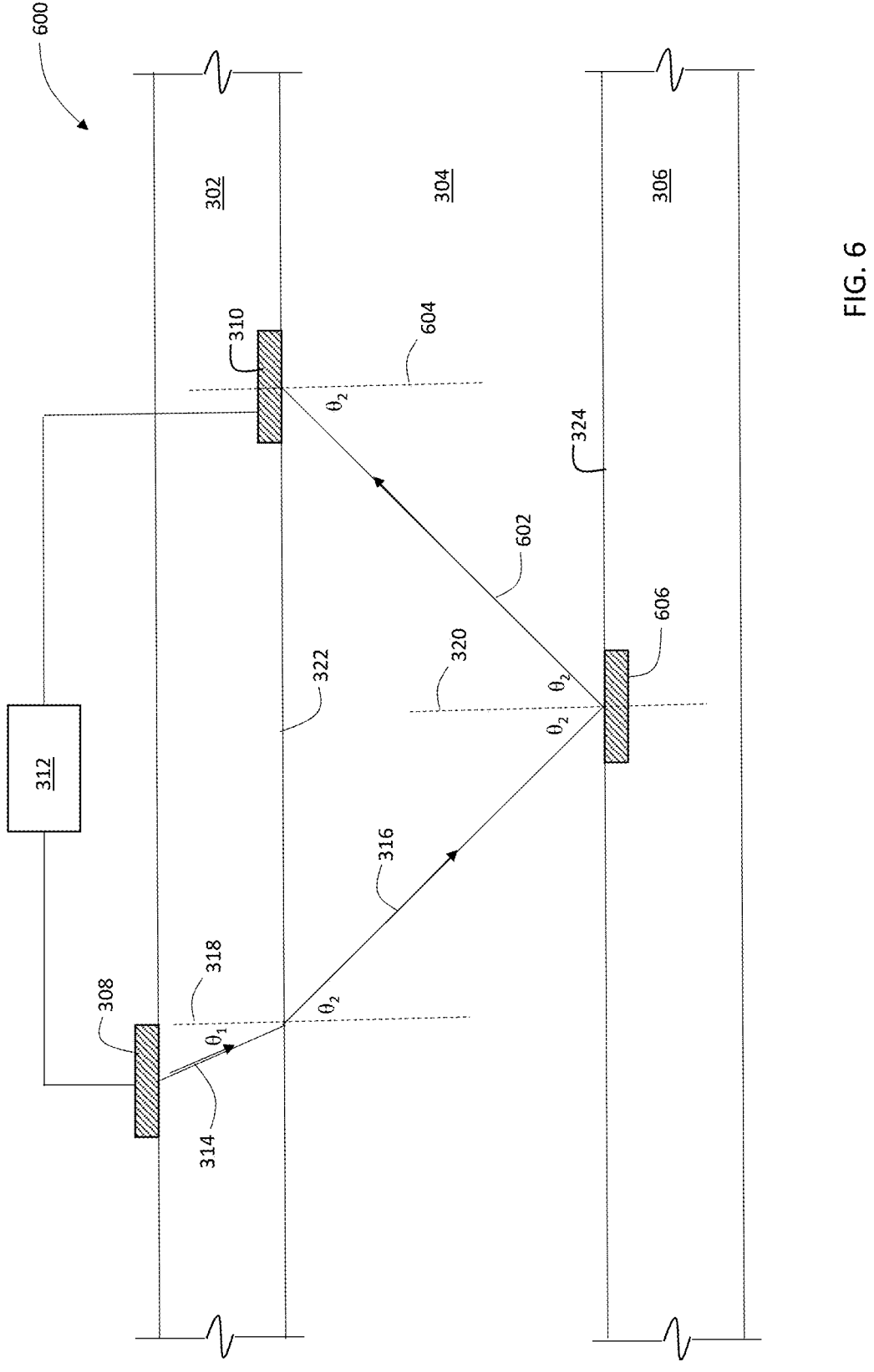
FIG. 6 is a schematic diagram showing a system for performing angle-resolved refraction measurements for a light beam in reflection mode.

In some embodiments, measurement system 300 can be configured to perform reflection mode measurements of the light beam refracted through solution 508. FIG. 6 is a schematic diagram showing a measurement system 600 for performing reflection mode measurements. System 600 includes light source 308, detector 310, and controller 312. Light source 308 is positioned to generate an incident light beam 314 that refracts at interface 322 as discussed previously in connection with FIG. 3, and is incident on interface 324 at an angle $\theta_2$ relative to interface normal 320.

In measurement system 600, mirror 606 is positioned to intercept refracted light beam 316 where it would otherwise cross interface 324. Mirror 606 reflects refracted beam 316, formed reflected beam 602 which reflects at an angle $\theta_2$ relative to normal 320. Reflected beam 602 is then incident on interface 322 at an angle $\theta_2$ relative to interface normal 604. At interface 322, reflected beam 602 is intercepted by detector 310, which measures the angle $\theta_2$. Due to the symmetry in measurement system 600, the angle $\theta_2$ of incidence of reflected beam 602 relative to normal 604 is the same as the angle of refraction of refracted beam 316 relative to normal 318. Consequently, Equations (12) and (13) remain valid for the reflection mode measurements performed by system 600, and calibration and quantitative concentration determination can be performed in the manner discussed above.

Solvent/Solute-Specific Calibration

In general, the calibration data that are measured are specific to the solute and solvent of interest, due to the complex, non-analytical relationship between the solution's refractive index $n_{solution}$ and solute concentration c. Accordingly, for each new combination of solute and solvent measurement systems 300 and 600 generally measure or retrieve a new set of calibration data that is specific to the solute and solvent of interest. In some embodiments, measurement systems 300 and 600 can each store multiple sets of calibration data, each set corresponding to a different combination of solute and/or solvent. When controller 312 receives an appropriate control signal from a control/logic unit in a bio-manufacturing system indicating that a particular combination of solute and solvent are to be measured, controller 312 retrieves an appropriate set of calibration data from storage unit 314, or measures a new set of calibration data specific to the solute and solvent combination.

It should be noted that the calibration data that is stored can take a number of forms. In some embodiments, the calibration data that is stored includes the measured data points $(c, \theta_2)$. In certain embodiments, the calibration data that is stored includes both the measured data points and values of the constants m and b determined for Equation (13). Conversely, in some embodiments, the calibration data that is stored includes only values of m and b; raw data points are not stored.

In general, the correlation between concentration c and refraction angle $\theta_2$ in Equation (13) (one example of which is plotted in FIG. 4) is approximately linear at relatively high solute concentrations, and more nonlinear at relatively lower solute concentrations. The exact nature of the correlation between c and $\theta_2$ is a complex function, and is dependent on the manner in which changes in solute concentration c cause changes in the refractive index $n_{solution}$, which in turn depends on the specific nature of interactions between the solute and solvent, as well as the refractive index of the pure solvent, $n_{solvent}$.

In Equation (13), the solute concentration c is assumed to depend linearly on the refraction angle $\theta_2$. However, as shown in FIG. 4, this linear relationship does not necessarily hold for all concentrations c. Thus, while assuming a linear relationship between c and $\theta_2$ is convenient for purposes of calibration and concentration calculation, more generally it can also be assumed in some embodiments that c is a nonlinear function of $\theta_2$. Moreover, a variety of nonlinear functional forms can be used to express c as a function of $\theta_2$. For example, in certain embodiments, c can be expressed as one or more of a polynomial function of $\theta_2$, a hyperbolic function of $\theta_2$, an exponential function of $\theta_2$, a logarithmic function of $\theta_2$, and a trigonometric function of $\theta_2$.

Where these or any other nonlinear functional forms are assumed for the relationship between c and $\theta_2$, controller 312 can use a variety of methods, including for example nonlinear regression analysis, to determine appropriate values of adjustable parameters of the assumed functional form. One advantage to storing measured data points $(c, \theta_2)$ in the calibration information is that controller 312 can readily change to a different assumption for the functional form governing the relationship between c and $\theta_2$. If the measured data points can be retrieved, and if the parameter values for the new functional form are not already present in the calibration information, controller 312 can determine the parameter values, e.g., by performing a regression analysis on the raw measured data points. Optionally, controller 312 can then update the calibration information by storing the parameter values.

As one example, consider Equation (6), where the concentration c is a linear function of $csc(\theta_r)$. At small angles, $csc(\theta_r) \approx 1/\theta_r$. Thus, for small $\theta_r$, $$c \approx m/\theta_r + b \qquad [14]$$

Accordingly, if the refraction angle $\theta_r$ is small, then c can be expressed as a linear function of $1/\theta_r$, with constants m and b having the values discussed above for Equation (6) That is, c can be expressed as a hyperbolic function of $\theta_r$ (or $\theta_2$), and a plot of c vs. $1/\theta_r$ may be approximately a straight line with slope m and y-intercept b.

Although the foregoing discussion focuses on determining the concentration c of a solute as a function of the measured refraction angle $\theta_2$, more generally other parameters can also be measured as a function of the refraction angle $\theta_2$. For example, in some embodiments, the pH of a solution can be determined as a general function g of the refraction angle:

$$pH = g(\theta_2) \qquad [15]$$

13
14

In general, pH can be a linear or non-linear function of the refraction angle, and can have any of the functional forms described herein in connection with the concentration c. Furthermore, Equation (15) can also be applied to other solution parameters that can be measured by the systems described herein including, but not limited to, pOH, viscosity, tonicity, osmolarity, and light scattering (e.g., light scattering intensity).

Reporting Information

As discussed above, the measurement systems disclosed herein can be used to measure solute concentrations for a wide variety of solute-solvent solution pairings. In general, solutions on which measurements are made include (but are not limited to) product solutions emerging from chromatography columns, bio-reactors, holding tanks, and other vessels in a biomanufacturing system. Alternatively, or in addition, the solutions can be intermediate solutions, effluents or eluents, or other liquid process streams from chromatography columns, bio-reactors, holding tanks, and other vessels in a biomanufacturing system.

Specific solutes for which concentration information can be quantitatively determined include proteins, polypeptides, amino acids, antibodies, and a variety of other biological molecules. In certain embodiments, the solute of interest is a recombinant therapeutic protein. Examples of such proteins include, but are not limited to, immunoglobulins (including light and heavy chain immunoglobulins, antibodies, or antibody fragments (e.g., any of the antibody fragments described herein), enzymes (e.g., a galactosidase (e.g., an alpha-galactosidase), Myozyme, or Cerezyme), proteins (e.g., human erythropoietin, tumor necrosis factor (TNF), or an interferon alpha or beta), or immunogenic or antigenic proteins or protein fragments (e.g., proteins for use in a vaccine). The recombinant therapeutic protein can be an engineered antigen-binding polypeptide that contains at least one multifunctional recombinant protein scaffold (see, e.g., the recombinant antigen-binding proteins described in Gebauer et al., Current Opin. Chem. Biol. 13:245-255, 2009; and U.S. Patent Application Publication No. 2012/0164066 (both incorporated herein by reference in their entirety)). Examples of recombinant therapeutic proteins that are antibodies include, but are not limited to: panitumumab, omalizumab, abagovomab, abciximab, actoxumab, adalimumab, adecatumumab, afelimomab, afutuzumab, alacizumab, alacizumab, alemtuzumab, alirocumab, altumomab, amatuximab, amatuximab, anatumomab, anrukinzumab, apolizumab, arcitumomab, atinumab, tocilizumab, basilizimab, bectumomab, belimumab, bevacizumab, besilesomab, bezlotoxumab, biciromab, canakinumab, certolizumab, cetuximab, cixutumumab, daclizumab, denosumab, densumab, eculizumab, edrecolomab, efalizumab, efungumab, epratuzumab, ertumaxomab, etaracizumab, figitumumab, golimumab, ibritumomab tiuxetan, igovomab, imgatuzumab, infliximab, inolimomab, inotuzumab, labetuzumab, lebrikizumab, moxetumomab, natalizumab, obinutuzumab, oregovomab, palivizumab, panitumumab, pertuzumab, ranibizumab, rituximab, tocilizumab, tositumomab, tralokinumab, tucotuzumab, trastuzumab, veltuzumab, zalutumumab, and zatuximab. Additional examples of recombinant therapeutic proteins that can be measured include: alglucosidase alfa, laronidase, abatacept, galsulfase, lutropin alfa, antihemophilic factor, agalsidase beta, interferon beta-la, darbepoetin alfa, tenecteplase, etanercept, coagulation factor IX, follicle stimulating hormone, interferon beta-la, imiglucerase, dornase alfa, epoetin alfa, insulin or insulin analogs, mecasermin, factov VIII, factor VIIa, anti-thrombin III, protein C, human albumin, erythropoietin, granulocute colony stimulating factor, granulocyte macrophage colony stimulating factor, interleukin-11, laronidase, idursuphase, galsulphase, α-1-proteinase inhibitor, lactase, adenosine deaminase, tissue plasminogen activator, thyrotropin alpha (e.g., Thyrogen®) and alteplase. Further examples of recombinant proteins that can be measured include acid α-glucosidase, alglucosidase alpha (e.g., Myozyme® and Lumizyme®), α-L-iduronidase (e.g., Aldurazyme®), iduronate sulfatase, heparan N-sulfatase, galactose-6-sulfatase, acid β-galactosidase, β-glucoronidase, N-acetylglucosamine-1-phosphotransferase, α-N-acetylgalactosaminidase, acid lipase, lysosomal acid ceramidase, acid sphingomyelinase, β-glucosidase (e.g., Cerezyme® and Ceredase®), galactosylceramidase, α-galactosidase-A (e.g., Fabrazyme®), acid β-galactosidase, β-galactosidase, neuraminidase, hexosaminidase A, and hexosaminidase B.

Because calibration data are used to establish an analytical relationship between solute concentration (or another parameter of interest) and the refractive index of the solution, values of the solute concentration can be determined using the methods and systems disclosed herein in real-time or near real-time, which can be important for feedback to, and control of, biomanufacturing processes. In particular, in some embodiments, the elapsed time between the initiation of a refractive index measurement and the time at which the solute concentration has been determined can be 1 minute or less (e.g., 30 seconds or less, 15 seconds or less, 10 seconds or less, 5 seconds or less, 3 seconds or less, 2 seconds or less, 1 second or less).

Concentration, pH, and any of the other foregoing types of information can be transmitted by controller 312 to another control/logic unit within a bio-manufacturing system for purposes of quality monitoring and feedback control of various process parameters and steps. As will be explained in greater detail in the next section, the transmitted information can be used for a variety of purposes, including to increase yields of valuable products, to reduce production of undesired by-products and waste streams, and to control rates of reactions occurring as part of the manufacturing process.

When implemented in particular as part of an in-line measurement system for continuous bio-manufacturing, the methods and systems disclosed herein can realize important advantages. For example, certain conventional measurement technologies such as UV absorbance and conductivity measurements can suffer from signal degradation/drift over time, and may require re-calibration relatively frequently to ensure accuracy. For continuous bio-manufacturing operations, however, re-calibration at frequent intervals may be highly inconvenient or even impossible, as nearly continuous process monitoring may be required. Reflection-based measurements and measurement systems, in contrast, typically do not suffer signal degradation/drift, and are therefore ideally suited for continuous manufacturing applications.

Integration with Bio-Manufacturing Systems

The measurement systems disclosed herein can be integrated with bio-manufacturing systems to provide feedback control to various components and steps in synthesis processes. As shown in FIG. 5, the measurement systems are typically implemented in-line between components of the manufacturing systems, so that flowing or stationary solutions can be analyzed in real time with no sampling or diversion. The measurement systems can also be used more conventionally with samples extracted from reaction vessels, holding tanks, or chromatography columns prior to performing refraction measurements.

Aspects of bio-manufacturing systems in addition to those described below are described in U.S. Pat. Nos. 9,650,412, 10,071,364, and 10,087,214, and in U.S. Patent Publications US 2018/0051054 and US 2020/0063082, the entire contents of each of which are incorporated by reference herein.

(a) Purification of Products and Intermediates

Integrated and fully continuous processes for manufacturing therapeutic protein drugs and other substances can include, e.g., providing a liquid culture medium containing a recombinant therapeutic protein that is substantially free of cells, then feeding the liquid culture medium into a first multi-column chromatography system (MCCS1). The next step involves capturing the recombinant therapeutic protein in the liquid culture medium using the MCCS1, and then continuously feeding the eluate of the MCCS1 containing the recombinant therapeutic protein into a second multi-column chromatography system (MCCS2), and purifying and polishing the protein using the MCCS2. The resulting eluate from the MCCS2 is considered a therapeutic protein drug substance. The processes are integrated and can run continuously from the liquid culture medium to the eluate from the MCCS2 that is the therapeutic protein drug sub stance.

Bio-manufacturing systems are typically used to perform the above processes. For example, such systems can include a MCCS1 that includes an inlet and a MCCS2 that includes an outlet. In these systems, the first and second MCCSs are in fluid communication with each other. The systems are also configured such that fluid can be passed into the inlet, through the first and second MCCSs, and exit the manufacturing system through the outlet.

Such systems can provide for continuous and time-efficient production of a therapeutic drug substance from a liquid culture medium. For example, the elapsed time between feeding a fluid (e.g., a liquid culture medium) containing a therapeutic protein into the first MCCS and eluting a therapeutic protein drug substance (containing the therapeutic protein) from the outlet of the second MCCS can be, e.g., between about 4 hours and about 48 hours.

Figure 7:
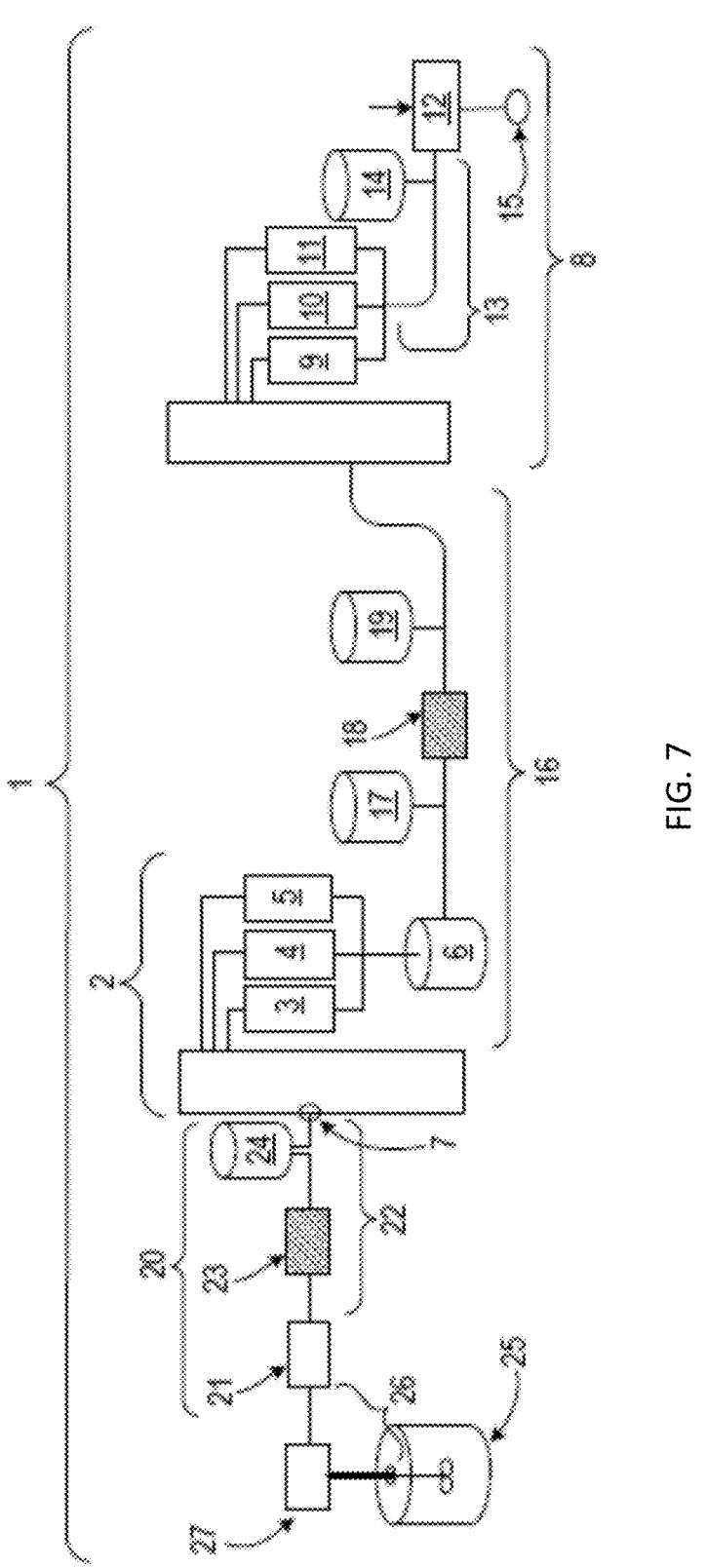
FIG. 7 is a schematic diagram of a continuous biological manufacturing system.

FIG. 7 is a schematic diagram showing an example of a bio-manufacturing system. System 1 includes a first MCCS, i.e., a four-column Periodic Counter-Current Chromatography System (PCCS) 2, where three of the four columns 3, 4, and 5 in four-column PCCS 2 perform the unit operation of capturing the recombinant therapeutic protein from a fluid containing the recombinant therapeutic protein (e.g., liquid culture medium that is substantially free of mammalian cells), and one of the columns 6 in PCCS 2 performs the unit operation of inactivating viruses present in the eluate from columns 3, 4, and 5 in PCCS 2 containing the recombinant therapeutic protein. Columns 3, 4, and 5 can contain a resin that utilizes a protein A-binding capture mechanism. Column 6 is capable of holding a fluid at a pH of about 3.75 for about 1 hour. PCCS 1 also has an inlet 7. Inlet 7 can be, e.g., an orifice that accepts entry of a fluid into PCCS 1.

System 1 also includes a second MCCS that is a PPCS 8 that includes three chromatography columns 9, 10, and 11 and one chromatographic membrane 12. Columns 9, 10, and 11 in PCCS 8 can contain a cationic exchange resin. Chromatographic membrane 12 in PCCS 8 can contain a cationic exchange resin. PCCS 8 also has a fluid conduit 13 disposed between columns 9, 10, and 11 in PCCS 8 and chromatographic membrane 12 in PCCS 8. PCCS 8 also has an in-line buffer adjustment reservoir 14 that is in fluid communication with fluid conduit 13, and is configured such that buffer contained within in-line buffer adjustment reservoir 14 is introduced into the fluid present in fluid conduit 13. PCCS 8 also includes an outlet 15. Outlet 15 can be, e.g., an orifice that allows exit of the fluid from PCCS 8.

System 1 can further include a fluid conduit 16 disposed between PCCS 2 and PCCS 8. System 1 can also include an in-line buffer adjustment reservoir 17 in fluid communication with fluid conduit 16 configured such that the buffer contained within in-line buffer adjustment reservoir 17 can be introduced into the fluid present in fluid conduit 16. System 1 can also include a filter 18 disposed in fluid conduit 16 to filter the fluid present in fluid conduit 16. System 1 can also include a break tank 19 disposed in fluid conduit 16 and configured to hold any fluid in fluid conduit 16 that cannot be readily fed into PCCS 8.

System 1 can further include a pump system 20 that is in fluid communication with inlet 7. Pump system 20 can include a pump 21 for pushing fluid into inlet 7. System 1 can also include a fluid conduit 22 disposed between pump 21 and inlet 7. System 1 can also include a filter 23 disposed in fluid conduit 22 to filter the fluid (e.g., liquid culture medium) present in fluid conduit 22. System 1 can also include a break tank 24 disposed in fluid conduit 22 configured such that break tank 24 is in fluid communication with fluid conduit 22 and is capable of storing any fluid present in fluid conduit 22 that is not able to enter inlet 7.

System 1 can also include a bioreactor 25 and a fluid conduit 26 disposed between bioreactor 25 and pump 21. A filtration system 27 may be disposed in fluid conduit 26 to filter (e.g., remove cells from) a liquid culture medium present in fluid conduit 26.

The first MCCS (PCCS 2) includes an inlet through which fluid (e.g., a liquid culture medium that is substantially free of cells) can be passed into the first MCCS. The inlet can be any structure known in the art for such purposes. It can include, e.g., a threading, ribbing, or a seal that allows for a fluid conduit to be inserted, such that after insertion of the fluid conduit into the inlet, fluid will enter the first MCCS through the inlet without significant seepage of fluid out of the inlet.

The first MCCS includes at least two chromatography columns, at least two chromatographic membranes, or at least one chromatography column and at least one chromatographic membrane, and an inlet. For example, the first MCCS can include a total of four chromatography columns, or three chromatography columns and one chromatographic membrane, or any of the other exemplary MCCSs described herein, or have one or more of any of the exemplary features of a MCCS (in any combination) described herein.

The chromatography column(s) and/or the chromatographic membrane(s) present in the first MCCS can contain one or more of a variety of resins. For example, the resin contained in one or more of the chromatography column(s) and/or chromatographic membrane(s) present in the first MCCS can be a resin that utilizes a capture mechanism (e.g., protein A-binding capture mechanism, protein G-binding capture mechanism, antibody- or antibody fragment-binding capture mechanism, substrate-binding capture mechanism, cofactor-binding capture mechanism, an aptamer-binding capture mechanism, and/or a tag-binding capture mechanism). The resin contained in one or more of the chromatography column(s) and/or chromatographic membrane(s) of the first MCCS can be a cation exchange resin, an anion exchange resin, a molecular sieve resin, or a hydrophobic interaction resin, or any combination thereof. Additional examples of resins that can be used to purify a recombinant therapeutic protein are known in the art, and can be contained in one or more of the chromatography column(s) and/or chromatographic membrane(s) present in the first MCCS. The chromatography column(s) and/or chromatography membranes present in the first MCCS can contain the same and/or different resins (e.g., any of the resins described herein or known in the art for use in recombinant protein purification).

The two or more chromatography column(s) and/or chromatographic resin(s) present in the first MCCS can perform one or more unit operations (e.g., capturing a recombinant therapeutic protein, purifying a recombinant therapeutic protein, polishing a recombinant therapeutic protein, inactivating viruses, adjusting the ionic concentration and/or pH of a fluid containing the recombinant therapeutic protein, or filtering a fluid containing a recombinant therapeutic protein). In non-limiting examples, the first MCCS can perform the unit operations of capturing a recombinant therapeutic protein from a fluid (e.g., a liquid culture medium) and inactivating viruses present in the fluid containing the recombinant therapeutic protein. The first MCCS can perform any combination of two of more unit operations described herein or known in the art.

The chromatography column(s) and/or chromatographic membrane(s) present in the first MCCS can be connected or moved with respect to each other by a switching mechanism (e.g., a column-switching mechanism). The first MCCS can also include one or more (e.g., two, three, four, or five) pumps (e.g., automated, e.g., automated peristaltic pumps). The column-switching events can be triggered by the detection of a level of recombinant therapeutic protein in the fluid passing through the first MCCS (e.g., the input into and/or eluate from one or more of the chromatography column(s) and/or chromatographic membranes in the first MCCS), a specific volume of liquid (e.g., buffer), or specific time elapsed. Column switching generally means a mechanism by which at least two different chromatography columns and/or chromatographic membranes in an MCCS (e.g., two or more different chromatography columns and/or chromatographic membranes present in an MCCS (e.g., the first or second MCCS)) are allowed to pass through a different step (e.g., equilibration, loading, eluting, or washing) at substantially the same time during at least part of the process.

PCCS 2 that is the first MCCS can include four chromatography columns, where the first three columns perform the unit operation of capturing a recombinant therapeutic protein from a fluid (e.g., a liquid culture medium), and the fourth column of the PCCS performs the unit operation of inactivating viruses in the fluid containing the recombinant therapeutic protein. A PCCS that is the first MCCS can utilize a column-switching mechanism. The PCC system can utilize a modified AKTA system (GE Healthcare, Piscataway, NJ) capable of running up to, e.g., four, five, six, seven, or eight columns, or more.

As discussed above, column switching events can be triggered by detection of a concentration of a particular protein or other substance in a fluid eluting from one of the columns of PCCS 2 or PCCS 8, flowing through a filter in the MCCS, contained in a break tank of the MCCS, or flowing through a conduit in the MCCS (e.g., between MCCS 1 and MCCS 2). The angle-resolved refraction measurement systems disclosed herein can be used to measure concentrations of such proteins, and to transmit the concentration information to a controller in system 1 that initiates events such as column switching, filtering, and fluid transport in system 1.

The first MCCS can be equipped with: one or more (e.g., two, three, four, five, six, seven, eight, nine, or ten) angle-resolved refraction measurement systems (e.g., systems 300, 600), one or more (e.g., two, three, four, five, six, seven, eight, nine, or ten) valves, one or more (e.g., two, three, four, five, six, seven, eight, nine, or ten) pH meters, and/or one or more (e.g., two, three, four, five, six, seven, eight, nine, or ten) conductivity meters. The first MCCS can also be equipped with a controller executing an operating system that utilizes software (e.g., Unicorn-based software, GE Healthcare, Piscataway, NJ) for determining when a column-switching should occur (e.g., based upon concentration information derived from refraction measurements, volume of liquid, or elapsed time) and affecting (triggering) the column-switching events. The angle-resolved refraction measurement systems can be placed optionally at the inlet of one or more (e.g., two, three, four, five, six, seven, eight, nine, or ten) of the chromatography column(s) and/or chromatographic membrane(s) in the first MCCS, and/or at the outlet of one or more of the chromatography column(s) and/or chromatography membrane(s) in the first MCCS.

The first MCCS can further include one or more (e.g., two, three, four, five, six, seven, eight, nine, ten, eleven, twelve, thirteen, fourteen, fifteen, sixteen, seventeen, eighteen, nineteen, twenty, twenty-one, twenty-two, twenty-three, or twenty-four) in-line buffer adjustment reservoir(s) and/or a buffer reservoir(s). In other examples, the first MCCS can include one or more (e.g., two, three, four, five, or six) break tanks that can hold fluid that cannot readily pass into one or more of the chromatography columns and/or chromatographic membranes in the first MCCS. The systems described herein can contain one or more break tanks (e.g., a break tank described herein) in the first and/or second MCCS. Other examples of the systems described herein do not include a break tank in the first MCCS or the second MCCS, or do not include a break tank in the entire system. Other examples of the systems include a maximum of one, two, three, four, or five break tank(s) in the entire system.

The second MCCS includes at least two chromatography columns, at least two chromatographic membranes, or at least one chromatography column(s) and at least one chromatographic membrane(s), and an outlet. For example, the second MCCS can include a total of four chromatography columns, three chromatography columns and one chromatographic membrane, or any of the other exemplary MCCSs described herein, or can have one or more of any of the exemplary features of an MCCS (in any combination) described herein. The chromatography column(s) and/or the chromatographic membrane(s) present in the second MCCS can have one or more of: any of the shapes, sizes, volumes (bed volumes), and/or unit operations described herein. The resin contained in one or more of the chromatography column(s) and/or chromatographic membrane(s) present in the second MCCS can be a resin that utilizes a capture mechanism (e.g., protein A-binding capture mechanism, protein G-binding capture mechanism, antibody- or antibody fragment-binding capture mechanism, substrate-binding capture mechanism, cofactor-binding capture mechanism, tag-binding capture mechanism, and/or aptamer-binding capture mechanism). Useful resins include, e.g., a cation exchange resin, an anion exchange resin, a molecular sieve resin, and a hydrophobic interaction resin. The chromatography column(s) and/or chromatography membranes present in the second MCCS can contain the same and/or different resins (e.g., any of the resins described herein or known in the art for use in recombinant protein purification).

The chromatography column(s) and/or chromatographic membrane(s) present in the second MCCS can perform one or more unit operations (e.g., any of the unit operations described herein or any combination of the unit operations described herein). In non-limiting examples, the second MCCS can perform the unit operations of purifying a recombinant therapeutic protein from a fluid and polishing the recombinant therapeutic protein present in the fluid containing the recombinant therapeutic protein. In other non-limiting examples, the second MCCS can perform the unit operations of purifying a recombinant therapeutic protein present in a fluid, polishing a recombinant therapeutic protein present in a fluid, and filtering a fluid containing a recombinant therapeutic protein. In another example, the second MCCS can perform the unit operations of purifying a recombinant therapeutic protein present in a fluid, polishing a recombinant therapeutic protein present in a fluid, filtering a fluid containing a recombinant therapeutic protein, and adjusting the ionic concentration and/or pH of a fluid containing a recombinant therapeutic protein. The second MCCS can perform any combination of two of more unit operations described herein or known in the art.

The second MCCS can also include one or more (e.g., two, three, four, or five) pumps (e.g., automated, e.g., automated peristaltic pumps).

The chromatography column(s) and/or chromatographic membrane(s) present in the second MCCS can be connected or moved with respect to each other by a switching mechanism (e.g., a column-switching mechanism). The column-switching events can be triggered by the detection of a level of recombinant therapeutic protein or other substance via angle-resolved reflectance measurements, as discussed above, to determine the level of recombinant therapeutic protein in the fluid passing through the second MCCS (e.g., the input into and/or eluate from one or more of the chromatography column(s) and/or chromatographic membranes in the second MCCS), a specific volume of liquid (e.g., buffer), or specific time elapsed.

The PCCS 8 that forms the second MCCS can contain three columns that perform the unit operation of purifying a recombinant therapeutic protein from a fluid, and a chromatographic membrane that performs the unit operation of polishing a recombinant therapeutic protein present in a fluid. For example, the three columns that perform the unit operation of purifying a recombinant therapeutic protein from a fluid can contain, e.g., a cationic exchange resin, and the chromatographic membrane that performs the unit operation of polishing can contain a cationic exchange resin. A PCCS that is the second MCCS can utilize a column-switching mechanism. For example, the PCCS can utilize a modified AKTA system (GE Healthcare, Piscataway, NJ) capable of running up to, e.g., four, five, six, seven, or eight columns, or more.

Similar to the first MCCS, the second MCCS can also be equipped with: one or more (e.g., two, three, four, five, six, seven, eight, nine, or ten) angle-resolved refraction measurement systems (e.g., systems 300 and/or 600), one or more (e.g., two, three, four, five, six, seven, eight, nine, or ten) valves, one or more (e.g., two, three, four, five, six, seven, eight, nine, or ten) pH meters, and/or one or more (e.g., two, three, four, five, six, seven, eight, nine, or ten) conductivity meters. The one or more angle-resolved refraction measurement systems transmit concentration information for the protein or other substance in the fluid that is measured to a controller that uses the concentration information to determine whether to trigger a column switching event. The second MCCS can be equipped with an operating system, executed by the controller that receives the concentration information, that utilizes software (e.g., Unicorn-based software, GE Healthcare, Piscataway, NJ) for determining when a column-switching event should occur (e.g., based upon angle-resolved refraction measurements, volume of liquid, or elapsed time) and initiating the column-switching events. In the examples where the second MCCS includes one or more angle-resolved refraction measurement systems, the refraction measurement systems can be placed optionally at the inlet of one or more (e.g., two, three, four, five, six, seven, eight, nine, or ten) of the chromatography column(s) and/or chromatographic membrane(s) in the second MCCS, and/or at the outlet of one or more of the chromatography column(s) and/or chromatography membrane(s) in the second MCCS.

The second MCCS can further include one or more (e.g., two, three, four, five, six, seven, eight, nine, ten, eleven, twelve, thirteen, fourteen, fifteen, sixteen, seventeen, eighteen, nineteen, twenty, twenty-one, twenty-two, twenty-three, or twenty-four) in-line buffer adjustment reservoir(s) and/or a buffer reservoir(s). In other examples, the second MCCS can include one or more (e.g., two, three, four, five, or six) break tanks (e.g., any of the break tanks described herein) that can hold fluid that cannot readily pass into one or more of the chromatography columns and/or chromatographic membranes in the second MCCS.

The second MCCS includes an outlet through which the therapeutic protein drug substance can exit the system. The outlet can include, e.g., a threading, ribbing, or a seal that allows for a fluid conduit to be inserted or a vial designed to contain or store the therapeutic protein drug substance. An outlet can contain a surface that can be used to seal a sterile vial or other such storage container onto the outlet in order to allow the recombinant protein drug product to flow directly into the sterile vial or storage container.

One or more angle-resolved refraction measurements systems, as disclosed herein, can also be positioned to measure the concentration of the protein drug substance (or another substance) flowing out of the outlet. This information can be transmitted to the MCCS controller, which can determine a purity of the substance based on the information.

The systems described herein can also include a fluid conduit that is disposed between the first MCCS and the second MCCS. One or more angle-resolved refraction measurement systems can be disposed along the fluid conduit to determine information (e.g., concentration information) about fluids held within (e.g., flowing through) the conduit. This information can be communicated to a MCCS controller which, as discussed above, can determine whether to initiate a column-switching event based on the information.

Any of the fluid conduits described herein can be, e.g., a tube that is made of, e.g., polyethylene, polycarbonate, or plastic. The fluid conduit disposed between the first MCCS and the second MCCS can further include one of more of the following in any combination: one or more in-line buffer adjustment reservoirs that are in fluid communication with the fluid conduit and are positioned such that the buffer stored within the in-line buffer adjustment reservoir(s) is added to the fluid present in the fluid conduit; a break tank (e.g., any of the break tank(s) described herein) that is in fluid communication with the fluid conduit and is positioned such that it can hold any excess fluid present in the fluid conduit that is unable to readily feed into the second MCCS; and one or more filters that are disposed in the fluid conduit such that they are capable of filtering (e.g., removing bacteria) the fluid present in the fluid conduit. Any of the in-line buffer adjustment reservoirs can contain, e.g., a volume of between about 0.5 L to 50 L of buffer (e.g., at a temperature at or below 25° C., 15° C., or 10° C.).

The systems described herein can optionally include a fluid conduit disposed between the final chromatography column or chromatographic membrane in the second MCCS and the outlet. The systems described herein can further include one or more filters in fluid connection with the fluid conduit disposed between the final chromatography column or chromatographic membrane in the second MCCS and the outlet, such that the filter can remove, e.g., precipitated material, particulate matter, or bacteria from the fluid present in the fluid conduit disposed between the final chromatography column or chromatographic membrane in the second MCCS and the outlet. Some examples of the systems provided herein also include a bioreactor that is in fluid connectivity with the inlet of the first MCCS. Any of the exemplary bioreactors described herein or known in the art can be used in the present systems.

Some examples of the systems provided herein also include a pump system. A pump system can include one or more the following: one or more (e.g., two, three, four, five, six, seven, eight, nine, or ten) pumps (e.g., any of the pumps described herein or known in the art), one or more (e.g., two, three, four, or five) filters (e.g., any of the filters described herein or known in the art), one or more (e.g., two, three, four, five, six, seven, eight, nine, or ten) UV detectors, and one or more (e.g., two, three, four, or five) break tanks (e.g., any of the break tanks described herein). Some examples of the systems provided herein further include a fluid conduit disposed between the pump and the inlet of the first MCCS (e.g., any of the exemplary fluid conduits described herein or known in the art). In some examples, this particular fluid conduit can include one or more (e.g., two, three, or four) pumps (e.g., any of the pumps described herein or known in the art) and/or one or more (e.g., two, three, or four) break tanks (e.g., any of the exemplary break tanks described herein), where these pump(s) and/or break tank(s) are in fluid connection with the fluid present in the fluid conduit.

Some examples of the systems described herein further include a further fluid conduit connected to the fluid conduit between the pump and the inlet, where one end of the further fluid conduit is fluidly connected to a bioreactor and the other end is fluidly connected to the fluid conduit between the pump and the inlet. This further fluid conduit can include a filter that is capable of removing cells from the liquid culture medium removed from the bioreactor (e.g., ATF cell retention system).

The foregoing bio-manufacturing systems allow for the continuous production of a therapeutic protein drug substance. For example, the systems provided herein allow for a percentage yield of recombinant therapeutic protein (from a starting material, e.g., a starting liquid culture medium) of greater than about 70%, greater than about 80%, greater than about 82%, greater than about 84%, greater than about 86%, greater than about 88%, greater than about 90%, greater than about 92%, greater than about 94%, greater than about 96%, or greater than about 98%. The systems described herein can also result in a percentage yield of recombinant therapeutic protein (from a starting material, e.g., a starting liquid culture medium) of between about 80% to about 90%, between about 82% to about 90%, between about 84% to about 90%, between about 84% to about 88%, between about 84% to about 94%, between about 82% to about 92%, or between about 85% to about 95%.

The systems described herein can also result in the production of a therapeutic protein drug substance that contains a concentration of recombinant therapeutic protein that is greater than about 1.0 mg/mL, greater than about 1.5 mg/mL, greater than about 2.0 mg/mL, greater than about 2.5 mg/mL, greater than about 3.0 mg/mL, greater than about 3.5 mg/mL, greater than about 4.0 mg/mL, greater than about 4.5 mg/mL, greater than about 5.0 mg/mL, greater than about 5.5 mg/mL, greater than about 6.0 mg/mL, greater than about 6.5 mg/mL, greater than about 7.0 mg/mL, greater than about 7.5 mg/mL, greater than about 8.0 mg/mL, greater than about 8.5 mg/mL, greater than about 9.0 mg/mL, greater than about 10.0 mg/mL, greater than about 12.5 mg/mL, or greater than about 15.0 mg/mL.

As discussed above, in some embodiments, the first and/or second MCCS can be a Periodic Counter-Current Chromatography System (PCCS). A PCCS can, e.g., include two or more chromatography columns (e.g., three columns or four columns) that are switched in order to allow for the continuous elution of recombinant therapeutic protein from the two or more chromatography columns. A PCCS can include two or more chromatography columns, two or more chromatographic membranes, or at least one chromatographic column and at least one chromatographic membrane. A column operation generally consists of the load, wash, elute, and regeneration steps. In PCCSs, multiple columns are used to run the same steps discretely and continuously in a cyclic fashion. Since the columns are operated in series, the flow through and wash from one column is captured by another column. This unique feature of PCCSs allows for loading of the resin close to its static binding capacity instead of to the dynamic binding capacity, as is typical during batch mode chromatography.

Figure 8:
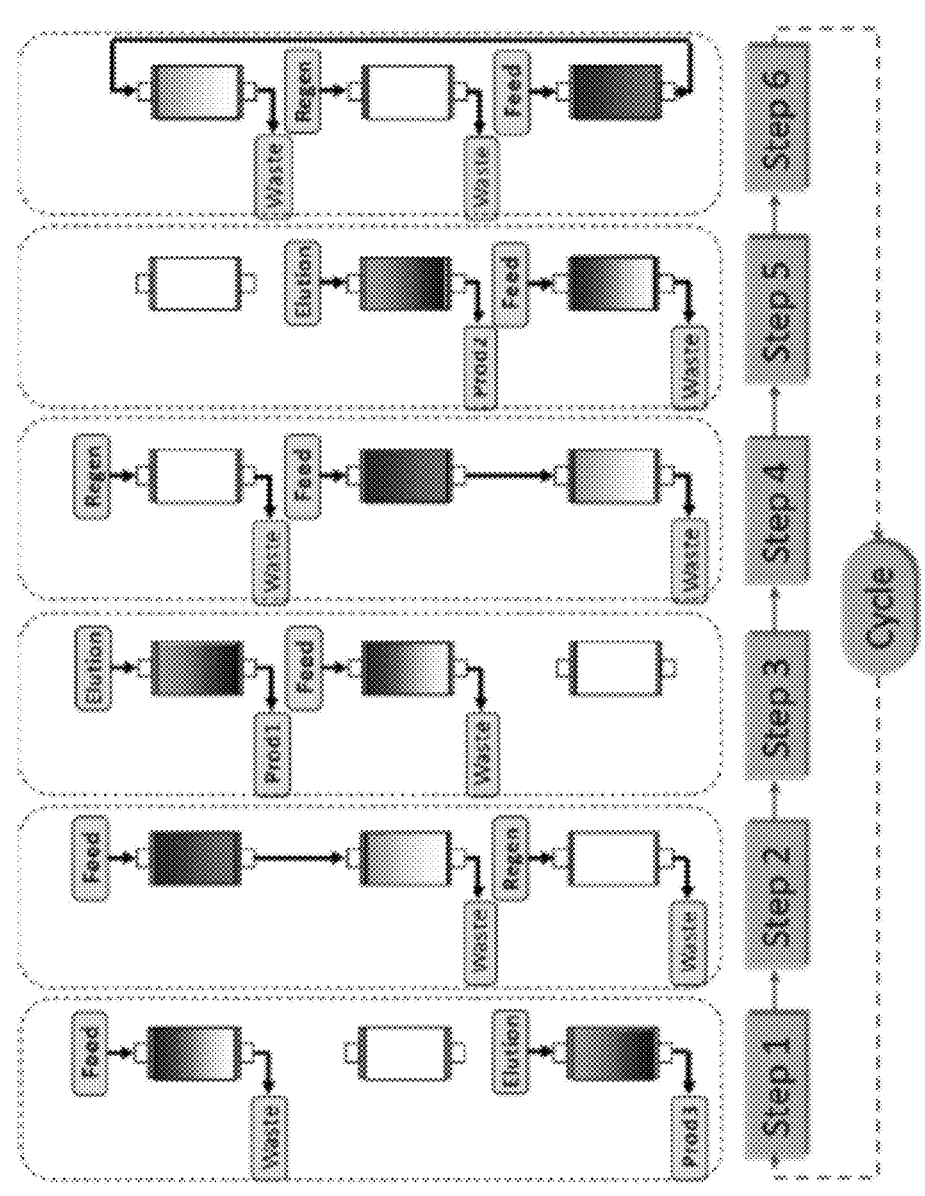
FIG. 8 is a schematic diagram showing steps in a chromatography column switching procedure for a continuous biological manufacturing system.

An example of the three column-switching technique used in a PCCS containing three columns is shown in FIG. 8. A cycle is defined as three complete column operations resulting in an elution pool from each of the three columns used in the column-switching technique. Once all the steps in the cycle are completed, the cycle is re-started. As a result of the continuous cycling and elution, fluid entering a PCCS is processed continuously, while recombinant therapeutic protein elution from each column is discrete and periodic.

To advance from one step to another in a PCCS cycle, such as the exemplary cycle shown in FIG. 8, a column-switching strategy is employed. The column switching method employs two automated switching operations per column in the three-columns in the exemplary PCCS system shown in FIG. 8, the first of which is related to the initial product breakthrough, while the second coincides with column saturation. The determination of when the column switching operations should take place is based on information about recombinant therapeutic protein concentrations in the eluate from each chromatography column in the PCCS.

As discussed above, the angle-resolved refraction measurement systems disclosed herein can be used to determine concentrations of recombinant therapeutic proteins in eluate from PCCS columns. The concentration information—which functions as a feedback control for the bio-manufacturing system—is transmitted to the MCCS controller, which initiates column switching after determining that a switch is warranted.

As an example, during column loading (Step 1; FIG. 3), the PCC control system can determine a baseline concentration of a therapeutic protein substance eluting from the column (which is typically zero concentration) using the angle-resolved refraction measurement systems discussed above. During active elution, as the protein substance breaks through (Step 2; FIG. 3), there is an increase (e.g., above the baseline concentration) in the measured protein concentration. The system continues to monitor the increasing protein concentration, and when the concentration reaches a pre-determined threshold value, the flow-through from column 1 is directed onto column 2 instead of to the waste. Nominally, this occurs at a time $t_1$.

As the feed continues into column 1, column 1 eventually becomes nearly saturated with the protein product. At this point, the measured concentration of protein in the eluate has reached another pre-determined value, which occurs at a time $t_2$. At this point, the MCCS controller switches the inlet feed to column 2.

The above column-switching strategy allows for the uniform loading of the columns irrespective of the feed product concentration and the capacity. Similar switches of the columns based on the level of recombinant protein detected in the eluate from each column can be implemented. Column switches can also be based on elapsed time or the amount of fluid (e.g., buffer) passed through the one or more chromatography column(s) and/or chromatographic membranes in the first or second MCCS.

In addition to providing feedback information to control column switching events, the angle-resolved refraction measurements systems disclosed herein can also provide feedback information for the adjustment of various other bio-manufacturing steps and operating parameters. One example of such adjustments is the controlled adjustment of buffer concentrations at various stages of the bio-manufacturing processes.

In general, one or more (e.g., three, four, five, six, seven, eight, nine, ten, eleven, twelve, thirteen, fourteen, fifteen, sixteen, seventeen, eighteen, nineteen, twenty, twenty-one, twenty-two, twenty-three, or twenty-four) different types of buffer can be employed during the use of the two or more MCCSs in any of the processes described herein. As is known in the art, the one or more types of buffer used in the two or more MCCSs used in the processes described herein will depend on the resin present in the chromatography column(s) and/or the chromatographic membrane(s) of the two or more MCCSs (e.g., the first and second MCCSs), the recombinant therapeutic protein, and unit operation (e.g., any of the exemplary unit operations described herein) performed by the specific chromatography column(s) and/or chromatography membranes of the two or more MCCSs. The volume and type of buffer employed during the use of the two or more MCCSs in any of the processes described herein can also be determined by one skilled in the art (e.g., discussed in more detail below). For example, the volume and type(s) of buffer employed during the use of the two or more MCCSs in any of the processes described herein can be chosen in order to optimize one or more of the following in the recombinant protein drug product: the overall yield of recombinant therapeutic protein, the activity of the recombinant therapeutic protein, the level of purity of the recombinant therapeutic protein, and the removal of biological contaminants from a fluid containing the recombinant therapeutic protein (e.g., absence of active viruses, mycobacteria, yeast, bacteria, or mammalian cells).

The unit operations of adjusting the ionic concentration and/or pH of a fluid containing the recombinant therapeutic protein can be performed using a MCCS (e.g., the first and/or second MCCS) that includes and utilizes a buffer adjustment reservoir (e.g., an in-line buffer adjustment reservoir) that adds a new or additional buffer solution into a fluid that contains the recombinant therapeutic protein (e.g., between columns within a single MCCS, or after the last column in a penultimate MCCS (e.g., the first MCCS) and before the fluid containing the recombinant therapeutic protein is fed into the first column of the next MCCS (e.g., the second MCCS). The in-line buffer adjustment reservoir can be any size (e.g., greater than 100 mL) and can contain any buffered solution (e.g., a buffered solution that has one or more of: an increased or decreased pH as compared to the fluid containing the recombinant therapeutic protein, an increased or decreased ionic (e.g., salt) concentration compared to the fluid containing the recombinant therapeutic protein, and/or an increased or decreased concentration of an agent that competes with the recombinant therapeutic protein for binding to resin present in at least one chromatographic column or at least one chromatographic membrane in an MCCS (e.g., the first or the second MCCS)).

(b) Upstream Identification, Verification, and Quantitative Measurements

Angle-resolved refraction measurements can be also be used in upstream (i.e., prior to obtaining a purified product) continuous bio-manufacturing operations. For example, in some embodiments, solutes of interest include components of buffer solutions that are used to maintain particular pH ranges within chromatography columns and bio-reactors. Concentrations of these buffer solution components can also be quantitatively determined. In addition, when buffer solution components are quantified, controller 312 can also calculate other information relating to a solution being measured, including the pH of the solution (i.e., based on the buffer composition).

In some embodiments, determination by the MCCS controller of the amount of buffer solution to add to process fluid is based on concentration information about a component of the process fluid derived from angle-resolved refraction measurements performed as discussed previously. For example, the solute for purposes of such measurements can be a buffer solution component or a component of the process fluid for which the concentration is related to the fluid buffer composition, the pH of the process fluid, and/or the ionic strength of the process fluid. Measurement of the concentration information for the component is provided as feedback information to the MCCS controller, which uses the feedback information to determine when and what quantity of one or more buffer solutions to discharge into the process fluid. Angle-resolved refraction measurement systems can generally be positioned at any location in the bio-manufacturing system (FIG. 7) for purposes of measuring process fluids to provide buffer-related feedback information to the MCCS controller.

In certain embodiments, angle-resolved refraction measurements can be used in in-line dilution, blending, and/or conditioning operations involving one or more buffer solutions. As an example, for operations involving quality control verification of buffer solutions, such measurements can be used to verify the identity of buffer solution components prior to blending the components to form a buffer solution. Similarly, such measurements can be used to verify the identity of one or more prepared buffer solutions before the solutions are introduced into a feed stream, blended with other solutions, injected into a bio-reactor, or otherwise introduced into a continuous bio-manufacturing system.

Buffer solution identification can also be performed using angle-resolved refraction measurements before buffer solutions are introduced onto chromatography columns for separation and/or purification of analytes, intermediates, and waste products.

Verification of the identities of components introduced into such systems can also be performed by angle-resolved refraction measurements for components other than buffers. Such components include, but are not limited to, anti-foaming agents, various types of reactor nutrients, and poloxamers (e.g., Pluronics, Synperonics, and/or Kolliphor).

To verify identities of buffer components, buffer solutions, and other components as described above, angle-resolved refraction measurements are typically compared to stored information (e.g., a library or database record) for the various substances. Typically, for example, a library record includes a set of calibration information that includes refraction angles and corresponding substance concentrations. Verification of the identity of a substance can occur by confirming that the measured angle of refraction at one or more measurement wavelengths corresponds to an angle (or a range of angles) associated with the substance in its library record. Such verifications can be performed automatically by the systems described herein, which can also generate an alert message (or execute other control functions) when the identity of a particular substance is not verified (e.g., the verification process fails).

In addition to verifying the identities of buffer components, buffers, and other components, angle-resolved refraction measurements can provide concentration information for these analytes as described above. This concentration information can be used in a variety of in-line dilution, blending, and conditioning processes that introduce buffers, agents, and other substances into a bio-manufacturing system at various points. For example, in some bio-manufacturing systems, one or more dosing pumps and/or flow meters with flow regulators are used to dynamically blend buffer components to form a buffer solution, which is then introduced in a feed stream into a bio-reactor. In addition to verifying the identities of the blended components as described above, angle-resolved refraction measurements provide feedback signals to a controller that regulates the dosing pumps to combine suitable amounts of each component to create a blended buffer solution that is constituted as desired. Measurements can be performed, for example, on stock solutions of the buffer components to determine the concentration of each prior to executing a blending operation.

In certain embodiments, angle-resolved refraction measurements can also be used to obtain concentration information for components during blending or dilution operations involving other substances including, but not limited to, growth media and nutrients such as iron. As described above, the identities and concentrations of these substances in blended and/or diluted solutions can be verified before the solutions are introduced into a feed stream for a bio-reactor.

As an example, in a perfusion bio-reactor, media feed is continuous over the course of a manufacturing run. Angle-resolved refraction measurements can be used as part of a feedback loop to regulate the amount of the growth medium that is introduced into a feed stream over time. A stock solution of growth medium can be metered (e.g., via a dosing pump or flow regulator) by a controller and combined with water and/or other components to generate a feed stream for delivery into a bio-reactor. Metering of the growth medium solution can be performed by a controller connected to the pump or regulator, which receives information about a concentration of the growth medium in the feed stream derived from angle-resolved refraction measurements.

In addition to confirming the concentration of the growth medium in the feed stream, such measurements can be used to dynamically adjust the amount of growth medium that is delivered to the bio-reactor over time. For example, as the cell population in the reactor increases, angle-resolved refraction measurements can be used to increase the amount of growth medium delivered to the reactor to support the larger cell population.

In some embodiments, angle-resolved refraction measurements can be used to provide feedback signals for filter selection during product filtration operations. For example, certain reaction products may be subjected to a diafiltration and/or ultrafiltration processes (e.g., a continuous diafiltration process) in which one or more molecular size-selective filters are used to separate reaction intermediates or products from reaction by-products and other substances in a product stream from a bio-reactor. Angle-resolved refraction measurements, performed as described above, can be used to identify reaction products or intermediates, and determine concentrations of these substances, on one or both sides of the filter(s). For example, such measurements can be used to confirm that target buffer, salt, and/or product concentrations have been achieved. Alternatively, or in addition, one or more filters can be adjusted (e.g., inserted or removed from the solution flow path) based on the measured concentrations of substances on one or both sides of the filter(s) to promote realization of target concentrations of products, buffers, and salt components.

As discussed above, angle-resolved refraction measurements can be used to measure concentrations of stock solutions, components, and other agents prior to blending of these substances to form feed stream solutions that are delivered into a bio-reactor and/or into one or more purification units downstream from a bio-reactor. Due to variability in the concentrations of stock solutions (which is relatively common), more precise control over the concentration of components in a final solution is achieved when measured concentration values are used for feedback control of dosing pumps and/or flow regulators during blending operations involving stock solutions and other substances.

Angle-resolved refraction measurements are particularly well suited for control of such operations due to the relatively high speed at which such measurements can be performed, and the absence of a requirement for routine calibration. Such methods are particularly useful for continuous bio-manufacturing operations, where calibration-related downtime is undesirable. In contrast, alternative measurement methods such as pH detection and conductivity monitoring typically exhibit calibration drift (for example, pH detection systems may need to be re-calibrated daily), and/or may not be sufficiently sensitive for purposes of determining identities and concentrations of some substances. Moreover, it has been observed that certain pH and conductivity sensors can be effectively "blinded" by some saline solutions, and therefore are difficult to use under certain bio-manufacturing conditions.

Further still, certain pH sensors include an electrolyte solution, and when such a sensor is used for in-line monitoring, the electrolyte solution can leak into the process stream in which the sensor is positioned, contaminating the stream and leading to inaccurate measurements. Some pH sensors also have specific storage requirements (such as immersive storage in solution), and therefore may necessitate interventional steps on the part of a system operator when the sensor is not in use, or when the sensor is activated for measurements. Angle-resolved measurements performed according to the systems and methods described above do not involve leaking electrolyte solutions or interventional steps to activate or de-activate sensors.

Conductivity-based measurements can be used to determine concentrations of buffer components. However, such measurements can be highly temperature dependent, and it has been observed that for certain buffers, a temperature change of even 1° C. can lead to conductivity changes of more than order of magnitude. To offset such changes, some conductivity-based measurement techniques use temperature compensation values to adjust conductivity measurements. However, such values typically only apply to a single component of a solution. Thus, a set of such values is generally used for a multi-component solution, and the set of values changes depending upon the deviation of the temperature from an ideal or baseline measurement temperature. Angle-resolved measurements performed according to the systems and methods described above are not affected by such temperature variations, and as a result, complex temperature-compensation calibration values need not be used to adjust the measurements. Instead, such measurements can be used with a temperature-independent set of calibration data to yield concentration values for multiple different analytes.

Angle-resolved refraction measurements can also be used to increase the efficiency and lower the cost of certain operational steps in a bio-manufacturing system. For example, as discussed above, following product generation, a product stream carrying one or products can be directed from a bio-reactor to one or more chromatography columns for purification and characterization. Columns used in this process are loaded with the product stream (or an eluent stream from another column), and components of the stream are separated and eluted in turn from the column. The column's productivity curve generally increases first and then decreases over time as the column is first loaded, then eluted.

During such operations, a column may typically be loaded to about 80% of capacity to ensure that the one or more products in the stream are not dumped from the downstream (i.e., elution) end of the column. However, this reduces the efficiency of the overall process, as about 20% of the column's loading capacity is not used. Further, additional quantities of any buffers used in the elution process are used, relative to the amounts that would have been used if the column was loaded closer to its full capacity.

Dynamic angle-resolved refraction measurements can be used to monitor the concentration of a product at the downstream end of the column to increase the load in the column, and thereby increase the efficiency of the purification process. Concentration measurements can be used to provide feedback signals to a pump or flow regulator that regulates the feed rate of the product stream so that feeding of the stream can be halted when the product is detected at the downstream end of the column. Once the product has been detected at the downstream end, the column has been loaded to its effective capacity, which ensures that the largest fraction of the column's nominal loading capacity is used.

Further still, detection of the column's temporal maximum loading end point can be used to trigger development of the column by flowing buffer solutions and other substances through the column as soon as the column has loaded (and, in some applications, equilibrated). In this manner, purification latency can be reduced and products derived from the product stream can be purified more efficiently.

Hardware and Software Implementations

Controller 312 can include one or more processors, one or more memory units, and one or more interfaces for interconnection with other components of the systems described herein. The interfaces can include wired and/or wireless interfaces for receiving information and transmitting information and control instructions to the components of the systems and other components and devices as described herein. Controller 312 is connected to storage unit 370 as shown in FIG. 5.

The processor(s) can process instructions for execution within the controller, including instructions stored in the one or more memory units and/or in storage unit 370. For example, the instructions can instruct the processor(s) to perform any of the analysis and control steps disclosed herein.

The memory unit(s) can store executable instructions for the processor(s), information about parameters of the systems, and measured information such as measured refraction and/or reflection angle information and measured refracted and/or reflected light intensities. Storage unit 370 can be a computer-readable medium, such as a floppy disk device, a hard disk device, an optical disk device, or a tape device, a flash memory or other similar solid state memory device, or an array of devices, including devices in a storage area network or other configurations. Storage unit 370 can store instructions that can be executed by the processor(s) described above, and any of the other information that can be stored by the one or more memory units.

In some embodiments, controller 312 can include a graphics processing unit to display graphical information (e.g., using a GUI or text interface) on an external input/output device. The graphical information can be displayed by a display device (e.g., a CRT (cathode ray tube) or LCD (liquid crystal display) monitor) for displaying any of the information disclosed herein. A user can use input devices (e.g., keyboard, pointing device, touch screen, speech recognition device) to provide input to controller 312.

A user of the systems described herein can provide a variety of different types of instructions and information to controller 312 via input devices. The instructions and information can include, for example, calibration information, information about one or more parameters being measured by the systems, and information about models used to correlate measured angles with a parameter. Controller 312 can use any of these various types of information to perform the methods and functions described herein. It should also be noted that any of these types of information can be stored (e.g., in storage unit 370) and recalled when needed by controller 312.

The methods, steps, and functions described herein can be implemented by controller 312 by executing instructions in one or more computer programs that are executable and/or interpretable by the controller 312. These computer programs (also known as programs, software, software applications or code) include machine instructions for a programmable processor, and can be implemented in a high-level procedural and/or object-oriented programming language, and/or in assembly/machine language. For example, computer programs can contain the instructions that can be stored in one or more memory units, in storage unit 370, and/or on a tangible, computer-readable medium, and executed by one or more processors of controller 312 as described above. As used herein, the term "computer-readable medium" refers to any computer program product, apparatus and/or device (e.g., magnetic discs, optical disks, memory, Programmable Logic Devices (PLDs), ASICs, and electronic circuitry) used to provide machine instructions and/or data to a programmable processor, including a machine-readable medium that receives machine instructions.

Alternatively, or in addition, the methods, steps, and functions described herein can be implemented, in full or in part, in hardware by electronic circuits and circuit elements that are specifically configured to perform the methods, steps, and functions. The circuits and circuit elements can be programmable or non-programmable. In certain embodiments, for example, the circuits can be application-specific integrated circuits (ASICs).

Other Embodiments

A number of embodiments have been described. However, other embodiments are understood by one of ordinary skill in the art to also fall within the scope of this disclosure and the following claims.

What is claimed is:

1. A method for controlling a biological manufacturing system, the method comprising:

directing a light beam to pass through a wall of a vessel or conduit containing a first fluid generated by the biological manufacturing system;

measuring an angle of refraction of the light beam in the first fluid, the angle of refraction corresponding to an angle between a propagation direction of the light beam in the first fluid and a normal to an interface between the vessel or conduit wall and the first fluid;

determining information about the first fluid based on the measured angle of refraction; and adjusting a parameter of the biological manufacturing system based on the information about the first fluid, wherein the parameter of the biological manufacturing system comprises a feed rate of a substance into a reactor of the system.

2. The method of claim 1, wherein the information about the first fluid comprises a concentration of a substance in the first fluid.

3. The method of claim 1, wherein the parameter of the biological manufacturing system further comprises at least one member selected from the group consisting of a fluid flow path that selectively directs a successive portion of the first fluid to one of multiple purification units of the system, a feed rate of a substance into a diafiltration unit of the system, a feed rate of a substance into a purification unit of the system, and a feed rate of successive portions of the first fluid into a purification unit of the system.

4. The method of claim 2, further comprising determining the concentration of the substance from a calibration equation derived from measured calibration data, wherein the calibration equation expresses the concentration as a function of the angle of refraction.

5. The method of claim 2, wherein the substance comprises at least one member selected from the group consisting of a protein, a recombinant protein-based drug product, and a nucleic acid-based product.

6. The method of claim 1, further comprising:

directing a second light beam to pass through a wall of a second vessel or conduit containing a second fluid generated by the biological manufacturing system;

measuring an angle of refraction of the second light beam in the second fluid, the angle of refraction corresponding to an angle between a propagation direction of the second light beam in the second fluid and a normal to an interface between the wall of the second vessel or conduit and the second fluid;

determining information about the second fluid based on the measured angle of refraction of the second light beam; and adjusting a second parameter of the biological manufacturing system based on the information about the second fluid, wherein the information about the second fluid comprises at least one member selected from the group consisting of a concentration of a buffer solution component in the second fluid and a concentration of an ionic compound or a dissolved salt thereof in the second fluid.

7. The method of claim 1, wherein the light beam is generated by a light source, and wherein the light source is integrated with the wall of the vessel or conduit; and which comprises directing the light beam generated by the light source to pass through the wall of the vessel or conduit at an angle relative to a normal to an interface between the vessel or conduit wall and the first fluid.

8. The method of claim 1, wherein the first fluid comprises an eluate solution from a first purification unit of the system and the information comprises a concentration of a substance in the first fluid, and wherein the parameter adjustment further comprises directing eluate solution from the first purification unit into an inlet of a second purification unit when the concentration of the substance in the first fluid exceeds a threshold value.

9. The method of claim 8, wherein the first and second purification units each comprise at least one chromatography column.

10. The method of claim 1, wherein the first fluid comprises an eluate solution from a first purification unit of the system, the information comprises a concentration of a substance in the first fluid, and an inlet of the first purification unit is connected to a conduit that delivers a feed solution to the first purification unit, the method further comprising, when a concentration of the substance in the first fluid exceeds a threshold value:

disconnecting the inlet of the first purification unit from the conduit; and connecting an inlet of a second purification unit of the system to the conduit to deliver the feed solution to the second purification unit.

11. The method of claim 1, wherein the information about the first fluid comprises a pH value of the first fluid.

12. The method of claim 1, wherein the first fluid comprises a fluid discharged from a purification unit of the system.

* * * * *